(12) United States Patent
Sathe et al.

(10) Patent No.: US 11,965,003 B2
(45) Date of Patent: Apr. 23, 2024

(54) RECOMBINANT LECTIN VARIANTS

(71) Applicant: Unichem Laboratories Ltd, Maharashtra (IN)

(72) Inventors: Dhananjay Sathe, Maharashtra (IN); Sudeep Kumar, Gujarat (IN)

(73) Assignee: UNICHEM LABORATORIES LTD, Maharashtra (IN)

( * ) Notice: Subject to any disclaimer, the term of this patent is extended or adjusted under 35 U.S.C. 154(b) by 484 days.

(21) Appl. No.: 17/272,090

(22) PCT Filed: Aug. 30, 2019

(86) PCT No.: PCT/IB2019/057314
§ 371 (c)(1),
(2) Date: Feb. 26, 2021

(87) PCT Pub. No.: WO2020/044296
PCT Pub. Date: Mar. 5, 2020

(65) Prior Publication Data
US 2021/0317171 A1    Oct. 14, 2021

(30) Foreign Application Priority Data
Aug. 31, 2018 (IN) .............................. 201821032765

(51) Int. Cl.
*C07K 14/42* (2006.01)
*A61K 38/00* (2006.01)

(52) U.S. Cl.
CPC .............. *C07K 14/42* (2013.01); *A61K 38/00* (2013.01)

(58) Field of Classification Search
CPC .................................. C07K 14/42; A61K 38/00
See application file for complete search history.

(56) References Cited

U.S. PATENT DOCUMENTS

| | | | |
|---|---|---|---|
| 9,500,650 B2 * | 11/2016 | Tateno | C07K 14/195 |
| 9,878,004 B2 * | 1/2018 | Williams | A61K 38/1767 |
| 10,463,711 B2 * | 11/2019 | Hamill | A61K 38/38 |
| 2015/0204870 A1 * | 7/2015 | Tateno | G01N 33/56966 435/7.1 |
| 2016/0317614 A1 * | 11/2016 | Williams | A61P 3/04 |
| 2016/0339078 A1 * | 11/2016 | Hamill | A61P 31/14 |

FOREIGN PATENT DOCUMENTS

| | | | | |
|---|---|---|---|---|
| WO | WO 2010/095143 | * | 8/2010 | |
| WO | WO-2010095143 A2 | * | 8/2010 | ............ C07K 14/37 |
| WO | WO-2013065302 A1 | * | 5/2013 | ........... C07K 14/195 |
| WO | WO 2014/203261 | * | 12/2014 | |

OTHER PUBLICATIONS

Peppa et al., 2015, Molecular Cloning, Carbohydrate Specificity and the Crystal Structure of Two Sclerotium rolfsii Lectin Variants, Molecules, 20: 10848-10865.*
Leonidas et al., 2007, Structural Basis for the Carbohydrate Recognition of the Sclerotium rolfsii Lectin, J Mol Biol, 368: 1145-1161.*

\* cited by examiner

*Primary Examiner* — Amber D Steele
(74) *Attorney, Agent, or Firm* — BACON&THOMAS,PLLC

(57) ABSTRACT

A modified lectin protein is provided having at least one amino acid modification in an amino acid sequence of SEQ ID NO. 1 orin an amino acid sequence having at least 60% homology thereto. The

RECOMBINANT LECTIN VARIANTS

CROSS REFERENCE TO RELATED APPLICATIONS

The application claims the benefit of PCT Appl. No. PCT/IB2019/057314, filed Aug. 30, 2019, the entire contents of which are incorporated herein by reference.

FIELD OF THE INVENTION

The present invention relates to a modified lectin protein and to a nucleic acid molecule comprising a nucleic acid sequence encoding the modified lectin protein. The invention also relates to a recombinant vector comprising such a nucleic acid molecule and to a transformed host cell comprising the recombinant vector. In addition, the invention relates to a pharmaceutical composition comprising the modified lectin protein and to the detection of a cancer cell, cancer diagnosis and to the treatment of cancer in a patient. The present invention also relates to a process for producing a recombinant *Sclerotium rolfsii* lectin protein.

BACKGROUND OF THE INVENTION

Lectins are highly specific carbohydrate-binding proteins, macromolecules that are highly specific for sugar moieties of other molecules. Lectins perform recognition on the cellular and molecular level and play numerous roles in biological recognition phenomena involving cells, carbohydrates, and proteins. They are divalent or polyvalent carbohydrate-binding proteins that bind and precipitate glycoproteins and agglutinate red blood cells. Lectins found in animals are most often found to aid in cell interactions, while plant lectins are known to ward off potential predators or pathogens.

Purified lectins are important in a clinical setting because they are used for blood typing. Some of the glycolipids and glycoproteins on an individual's red blood cells can be identified by lectins. Many lectins are used as biomarkers indicating early detection of malignant growth or as autophagy inducers while other lectins also show the ability to inhibit cancerous growth through apoptosis. Due to unregulated cell proliferation, some of the carbohydrate moieties are expressed as an antigen on cancerous cells. Lectins are used as a drug delivery agent in cancer therapy because they bind specifically to the malignant tumours. Further since the lectins also modulate cancer associated pathways they have potential as cancer diagnostic and therapeutic agents.

There are several antigens to which lectins bind and which have been characterised on the cancer cell surface; most of the antigens are specific for a particular type of cancer and lectin-binding to these antigens can result in inhibition of cancerous growth through inducing apoptosis in the cancerous cells. Currently, most commercially available lectins are from plants and other eukaryotes.

*Sclerotium rolfsii* lectin (SRL) is a lectin that has been isolated from the sclerotial bodies of the soil-borne phytopathogenic fungus *S. rolfsii*. SRL has specificity towards Thomsen-Friedenreich (TF) antigen and Tn antigen. TF antigen is a disaccharide (Galβ1→3GalNAc-α-Ser/Thr) that is overexpressed on the cell surface of various different human cancer cells. Tn antigen is a monosaccharide (GalNAc-α-). Due its specificity for TF and Tn antigen, SRL has been shown to bind to human colon cancer, ovarian cancer and leukaemic cells. The crystal structure of SRL has been determined (Leonidas et al., J Mol Biol. 2007 May 11; 368(4):1145-61), but experimental validation of the carbohydrate binding sites identified from the crystal structure has not been performed.

Whilst the lectins offer many advantages as anti-cancer tools, they still carry with them many limitations such as a lack of selectivity, inconsistent quality and performance and the production not being readily scalable. Moreover, the plant-derived lectins have often been reported to bind to a range of different glycan structures and so lack the selectivity required for many applications. Also the batch-to-batch variability is common when using plant lectins. The quality of the products depends on the methodology of isolation of the plant material, and on the quality of the starting plant material itself.

Isolation of lectin from the natural sources is not reliable because the lectin so obtained lacks in consistency with respect to the desired properties. Further isolating proteins from natural sources is an expensive and difficult process. The techniques used to isolate the naturally occurring lectins usually provide very low yields especially if the protein is only present at low concentrations. Also they are occasionally unable to distinguish between isoforms of the same lectin. Therefore, they are obtained as mixtures, which provide a large range of uncertainty. In this sense, the production of recombinant lectins by recombinant DNA (rDNA) techniques has the advantage of providing single proteins, with better and consistent yields having precise characterisation in drastically less amount of time and at the same time being readily scalable. By using rDNA technology one can transfer the gene that produces the protein of interest into a suitable host. The protein then can be produced and isolated with less time and effort as compared with the traditional methods.

WO 2010/095143 discloses recombinant lectin variants Rec-2 and Rec-3, which are derived from the native SRL sequence by the substitution of 3 or 5 amino acids respectively. The crystal structure of these variants has been reported (Peppa et al., Molecules. 2015 Jun. 12; 20(6): 10848-65).

WO 2014/203261 discloses a recombinant lectin variant derived from the native SRL sequence by the substitution of 12 amino acids.

There remains a need for further lectin variants which exhibit alternative properties. In particular, it is advantageous for lectins that are to be used in cancer diagnosis and as therapeutic agents to be soluble and stable without compromising on their specific affinity towards the malignant tumours/cancer cells. Therefore, there is a need for new recombinant lectin sequences and efficient methods to produce the recombinant lectins having sufficient levels of transgene expression in the appropriate host cells and having solubility and/or stability whilst also retaining the affinity towards malignant cells.

The present invention seeks to address one or more of the above needs.

SUMMARY OF THE INVENTION

According to an aspect of the present invention, there is provided a modified lectin protein comprising an amino acid sequence selected from:
i) SEQ ID NO. 1; or
ii) an amino acid sequence having at least 60% homology to i), wherein the amino acid sequence of i) or ii) comprises at least one amino acid modification selected from one of more of the following (a) to (d):
  a) at least one amino acid modification in a carbohydrate binding site of i) or ii);
  b) at least one amino acid modification in the N-terminus of i) or ii), wherein cleavage of an initiator methionine is increased as compared with the amino acid sequence of i);
  c) at least one amino acid modification that reduces dimer formation of the modified lectin protein as compared with a lectin protein of SEQ ID NO. 1; or
  d) at least one amino acid modification that reduces oxidation of the modified lectin protein as compared with a lectin protein of SEQ ID NO. 1.

In some embodiments, the modified lectin protein does not consist of the amino acid sequence of any of SEQ ID NOS. 2 to 4. In some further embodiments, the modified lectin protein has a cytotoxic effect.

According to an aspect of the present invention, there is provided a modified lectin protein, wherein the modified lectin protein comprises an amino acid sequence selected from any one of:
  i) SEQ ID NO. 1; or
  ii) an amino acid sequence having at least 60% homology to i),
  wherein the amino acid sequence of i) or ii) comprises at least one amino acid modification selected from one of more of the following (a) to (d):
    a. at least one amino acid modification in a carbohydrate binding site of i) or ii); or
    b. at least one amino acid modification in an N-terminus of i) or ii),
    c. at least one amino acid modification at position 76; or
    d. at least one amino acid modification at position 44 or 89,
  wherein the modified lectin protein does not consist of the amino acid sequence of any of SEQ ID NOS. 2 to 4.

According to another aspect of the invention there is provided a modified lectin protein, wherein the modified lectin protein comprises an amino acid sequence selected from any one of:
  i) SEQ ID NO. 1; or
  ii) an amino acid sequence having at least 60% homology to i),
  wherein the amino acid sequence of i) or ii) comprises at least one amino acid modification selected from one of more of the following (a) to (d):
  a) at least one amino acid modification in a carbohydrate binding site of i) or ii); or
  b) at least one amino acid modification in the N-terminus of i) or ii), wherein cleavage of an initiator methionine is increased as compared with the amino acid sequence of i);
  c) at least one amino acid modification that reduces dimer formation of the modified lectin protein as compared with a lectin protein of SEQ ID NO. 1 at position 76; or
  d) at least one amino acid modification that reduces oxidation of the modified lectin protein as compared with a lectin protein of SEQ ID NO. 1 at position 44 or 89, wherein the modified lectin protein does not consist of the amino acid sequence of any of SEQ ID NOS. 2 to 4.

Optionally, a modified lectin protein of the invention has a biological activity.

In one embodiment, the modified lectin protein comprises an amino acid sequence having at least 70%, 80%, 90%, 95%, 97% or 99% homology to SEQ ID NO. 1.

According yet another aspect of the present invention, there is provided a modified lectin protein comprising an amino acid sequence selected from:

i. SEQ ID NO. 1; or ii. an amino acid sequence having at least 60% homology to i), wherein the amino acid substitution is selected from one or more of:

a. an amino acid substitution in the primary carbohydrate binding site, wherein the substituting amino acid is selected from one or more of:

i. a non-polar, polar, acidic or basic amino acid at position 27 and/or at position 28;

ii. a non-polar amino acid at position 47 and/or a polar amino acid at position 48;

iii. a non-polar amino acid at position 70, a polar amino acid at position 71 and/or a non-polar amino acid at position 72; and/or iv. any other amino acid at position 105, b. an amino acid substitution in the secondary carbohydrate binding site, wherein the substituting amino acid is selected from one or more of:

i. a non-polar amino acid at position 77, a non-polar amino acid at position 78 and/or a polar amino acid at position 80;

ii. any other amino acid at position 101;

iii. a non-polar amino acid at position 112; and/or a polar amino acid at position 114.

In another embodiment, the modified lectin protein comprises at least one amino acid modification in a carbohydrate binding site of i) or ii).

In some embodiments, the carbohydrate binding site is a primary and/or a secondary carbohydrate binding site.

In one embodiment, the primary carbohydrate binding site comprises a position selected from one or more of: 27, 28, 47, 48, 70, 71, 72 and 105 in SEQ ID NO. 1 or a corresponding position in a sequence having at least 60%, 70%, 80%, 90%, 95%, 97% or 99% homology thereto.

In one such embodiment, the position of the amino acid modification is selected from one or more of:

i) 27 and/or 28;

ii) 47 and/or 48;

iii) 70, 71 and/or 72; and/or iv) 105.

In another embodiment, the secondary carbohydrate binding site comprises a position selected from one or more of: 77, 78, 80, 101, 112 and 114 in SEQ ID NO. 1 or a corresponding position in the sequence having at least 60%, 70%, 80%, 90%, 95%, 97% or 99% homology thereto.

In one such embodiment, the position of the amino acid modification is selected from one or more of:

i) 77, 78 and/or 80;

ii) 101;

iii) 112 and/or 114.

In yet another embodiment, the amino acid modification is an amino acid substitution such that a substituting amino acid replaces an original amino acid. In one embodiment, the amino acid substitution is a conservative or favourable amino acid substitution.

In one embodiment, the amino acid substitution in the primary carbohydrate binding site is selected from one or more of:

i) at position 27: a conservative, favourable or unfavourable amino acid, wherein the conservative amino acid is non-polar or acidic; favourable is polar or basic and unfavourable amino acid is non-polar;
ii) at position 28: a conservative, favourable, neutral or unfavourable amino acid, wherein the conservative amino acid is non-polar; favourable is polar, neutral is acidic or basic and unfavourable amino acid is polar;
iii) at position 47: an unfavourable amino acid, which is basic or non-polar;
iv) at position 48: an unfavourable amino acid, which is non-polar;
v) at position 70: an unfavourable amino acid, which is non-polar;
vi) at position 71: an unfavourable amino acid, which is non-polar;
vii) at position 72: an unfavourable amino acid, which is non-polar; and/or viii) at position 105: a conservative, favourable, neutral or unfavourable amino acid, wherein the conservative amino acid is basic or non-polar; favourable is polar, neutral is acidic, basic or polar and/or unfavourable amino acid is polar, non-polar or acidic.

In another embodiment, the amino acid substitution in the secondary carbohydrate binding site is selected from one or more of:
i) at position 77: an unfavourable amino acid which is non-polar;
ii) at position 78: an unfavourable amino acid which is non-polar;
iii) at position 80: an unfavourable amino acid which is non-polar;
iv) at position 101: a favourable, an unfavourable or a neutral amino acid, wherein the favourable amino acid is polar or basic, the unfavourable amino acid is non-polar and the neutral amino acid is non-polar or acidic;
v) at position 112: an unfavourable amino acid which is non-polar;
vi) at position 114: an unfavourable amino acid which is polar.

In one embodiment, the modified lectin protein comprises at least one amino acid modification in the N-terminus of i) or ii), wherein the N-terminus comprises a position selected from: 1 and/or 2 in SEQ ID NO. 1 or a corresponding position in the sequence having at least 60%, 70%, 80%, 90%, 95%, 97% or 99% homology thereto.

In one embodiment, the amino acid modification is an amino acid substitution at position 1 wherein a substituting amino acid is not threonine or valine. In further embodiments, the substituting amino acid is selected from: alanine, glycine, proline or serine. In further still embodiments, the amino acid modification is an amino acid substitution at position 2 wherein a substituting amino acid is tryptophan.

In some embodiments, cleavage of an initiator methionine is increased or decreased as compared with a control.

In another embodiment, the amino acid modification at position 76 is an amino acid substitution with a non-polar amino acid. In some embodiments, the non-polar amino acid is selected from: glycine, valine or leucine.

In one embodiment, the amino acid modification at position 44 or 89 is an amino acid substitution with a non-polar amino acid. In some embodiments, the amino acid modification is preferably at position 89. In some embodiment, the non-polar amino acid is selected from: leucine, isoleucine or valine.

In another embodiment, the modified lectin protein is soluble, partially soluble or insoluble and/or has cytotoxicity. In some embodiments, the modified lectin protein has a cytotoxicity that is at least 10%, 20%, 30%, 40%, 50%, 60%, 70%, 80%, or 90% of a control. In an alternative embodiment, the modified lectin protein has a percentage cytotoxicity that is less than 10% of a control, or is absent of cytotoxicity. In another alternative embodiment, the modified lectin protein has a percentage cytotoxicity that is at least a 10%, 20%, 30%, 40%, 50%, 60%, 70%, 80%, 90%, or 100% increase compared with that of a control.

In yet another embodiment, the modified lectin protein is equal to or less than 500, 400, 300, 250, 200, or 150 amino acids in length.

According to further aspect of the present invention, there is provided a pharmaceutical composition comprising a modified lectin protein and a pharmaceutically acceptable diluent or excipient and optionally a further therapeutic ingredient. There is also provided a method of treatment of cancer in a patient comprising administering the modified lectin protein or the pharmaceutical composition of modified lectin protein to the patient.

According to another aspect of the invention, there is provided a pharmaceutical composition comprising a modified lectin protein as described above and a pharmaceutically acceptable diluent or excipient and optionally a further therapeutic ingredient. According to a further aspect of the invention, there is provided a method of treatment of cancer in a patient comprising administering the modified lectin protein as described above to a patient. In some embodiments, the method comprises administering the pharmaceutical composition described above to a patient.

According to yet another aspect of the present invention, there is provided a modified lectin protein or the pharmaceutical composition of modified lectin protein for use in the treatment of cancer. Further there is provided a modified lectin protein used in the detection of a cancer cell, cancer diagnosis and/or cancer therapy.

According to a further aspect of the invention, there is provided a modified lectin protein as described above for use in medicine. Alternatively, there is provided a pharmaceutical composition as described above for use in medicine. In some embodiments, the modified lectin protein or the pharmaceutical composition as described above are for use in the treatment of cancer. According to a further aspect of the invention, there is provided the modified lectin protein as described above when used in the detection of a cancer cell, cancer diagnosis and/or cancer therapy.

According to an aspect of the present invention, there is provided a nucleic acid molecule comprising a nucleotide sequence encoding a modified lectin protein, wherein the modified lectin protein comprises an amino acid sequence selected from:
i) SEQ ID NO. 1; or
ii) an amino acid sequence having at least 60% homology to i),
and wherein the amino acid sequence of i) or ii) comprises at least one amino acid modification selected from one of more of the following (a) to (d):
a) at least one amino acid modification in a carbohydrate binding site of i) or ii);
b) at least one amino acid modification in the N-terminus of i) or ii);
c) at least one amino acid modification at position 76; or
d) at least one amino acid modification at position 44 or 89, According to another aspect of the present invention, there is provided a nucleic acid molecule comprising a nucleotide sequence encoding a modified lectin protein, wherein the modified lectin protein comprises an amino acid sequence selected from:

i) SEQ ID NO. 1; or
ii) an amino acid sequence having at least 60% homology to i),
and wherein the amino acid sequence of i) or ii) comprises at least one amino acid modification selected from one of more of the following (a) to (d):
a) at least one amino acid modification in a carbohydrate binding site of i) or ii);
b) at least one amino acid modification in the N-terminus of i) or ii), wherein cleavage of an initiator methionine is increased as compared with the amino acid sequence of i);
c) at least one amino acid modification that reduces dimer formation of the modified lectin protein as compared with a lectin protein of SEQ ID NO. 1; or
d) at least one amino acid modification that reduces oxidation of the modified lectin protein as compared with a lectin protein of SEQ ID NO. 1.

According to another aspect of the invention, there is provided a nucleic acid molecule comprising a nucleotide sequence encoding a modified lectin protein as described above. In a further aspect of the invention there is provided a recombinant vector comprising an insert of this nucleic acid molecule.

In some embodiments, the vector operatively linked in a 5' to 3' direction: comprises a promoter which functions in a host cell; a nucleotide sequence as described above encoding a modified lectin protein; and a termination signal. In another embodiment, the recombinant vector is capable of being replicated, transcribed, translated and/or expressed in a unicellular organism.

In yet another aspect of the invention, there is provided a transformed host cell comprising the nucleic acid molecule described above. In some embodiments, the host cell is an *Escherichia coli* bacterium or a yeast cell.

According to another aspect of the present invention, there is provided a recombinant vector comprising an insert of a nucleic acid molecule, wherein the nucleic acid molecule comprises nucleotide sequence encoding a modified lectin protein comprising an amino acid sequence selected from:
i) SEQ ID NO. 1; or
ii) an amino acid sequence having at least 60% homology to i), and wherein the amino acid sequence of i) or ii) comprises at least one amino acid modification selected from one of more of the following (a) to (d):
a) at least one amino acid modification in a carbohydrate binding site of i) or ii);
b) at least one amino acid modification in the N-terminus of i) or ii);
c) at least one amino acid modification at position 76; or
d) at least one amino acid modification at position 44 or 89.

According to another aspect of the present invention, there is provided a recombinant vector comprising an insert of a nucleic acid molecule, wherein the nucleic acid molecule comprises nucleotide sequence encoding a modified lectin protein comprising an amino acid sequence selected from:
i) SEQ ID NO. 1; or
ii) an amino acid sequence having at least 60% homology to i),
and wherein the amino acid sequence of i) or ii) comprises at least one amino acid modification selected from one of more of the following (a) to (d):
a) at least one amino acid modification in a carbohydrate binding site of i) or ii);
b) at least one amino acid modification in the N-terminus of i) or ii), wherein cleavage of an initiator methionine is increased as compared with the amino acid sequence of i);
c) at least one amino acid modification that reduces dimer formation of the modified lectin protein as compared with a lectin protein of SEQ ID NO. 1; or
d) at least one amino acid modification that reduces oxidation of the modified lectin protein as compared with a lectin protein of SEQ ID NO. 1.

In a final aspect of the invention, there is provided a method for producing a recombinant *Sclerotium rolfsii* lectin protein comprising:
i) culturing a host cell containing the recombinant vector as described above coding for a recombinant lectin protein;
ii) expressing the recombinant lectin protein;
iii) isolating a crude recombinant lectin protein from the culture.

Brief Description of the Accompanying Sequences

SEQ ID NO. 1: represents the native *S. rolfsii* lectin amino acid sequence.

SEQ ID NO. 2: represents a variant of the *S. rolfsii* lectin amino acid sequence (reported as Rec-2 in WO 2010/095143).

SEQ ID NO. 3: represents a variant of the *S. rolfsii* lectin amino acid sequence (reported as Rec-3 in WO 2010/095143).

SEQ ID NO. 4: represents a variant of the *S. rolfsii* lectin amino acid sequence (reported in WO 2014/203261).

DETAILED DESCRIPTION OF THE INVENTION

Definitions

The term "protein" as used herein refers to a polymer of amino acid residues.

The term "lectin" as used herein refers to a carbohydrate-binding protein.

The term "modified lectin protein" as used herein refers to a polymer of amino acid residues that has carbohydrate-binding activity and that contains at least one amino acid modification.

The term "amino acid" as used herein refers to naturally occurring and synthetic amino acids, as well as amino acid analogues and amino acid mimetics that have a function that is similar to the naturally occurring amino acids. Naturally occurring amino acids are those encoded by the genetic code and include the proteinogenic amino acids. Naturally occurring amino acids also include those modified after translation in cells. Synthetic amino acids include non-canonical amino acids such as selenocysteine and pyrrolysine. Typically synthetic amino acids are not proteinogenic amino acids.

The term "amino acid modification" as used herein refers to the addition, deletion or substitution of an amino acid at a particular position in an amino acid sequence. In one embodiment, the addition of an amino acid refers to the addition of at least 1, 2, 3, 4 or 5 amino acids at a particular position in an amino acid sequence. The processes of addition, deletion or substitution are carried out as per present invention or as per methods known to skilled person. In one embodiment, "amino acid modification" as used herein refers to one or more modifications selected from: acetylation, nitration, glycation and/or sulphonation.

The term "amino acid substitution" as used herein refers to the replacement of an amino acid at a particular position in an amino acid sequence. The term "amino acid substitution" encompasses both conservative and non-conservative amino acid substitutions. A conservative amino acid substitution provides a functionally similar amino acid. In other words, the amino acid that replaces the original amino acid (i.e. the "substituting" amino acid) has similar biochemical properties. A non-conservative substitution provides a functionally dissimilar amino acid. In other words, the amino acid that replaces the original amino acid (i.e. the "substituting" amino acid) has different biochemical properties. In one embodiment, the amino acid substitution is a "favourable" amino acid substitution. A favourable amino acid substitution preserves a biological function and/or other property of the modified lectin protein. In another embodiment both conservative and favourable amino acid substitutions are based on pairwise or a multiple sequence alignment of lectin proteins. The conservative substitution is the substitution with amino acid that occurs in maximum natural lectin proteins at corresponding position and the favourable substitution is the substitution with amino acid that occurs in few natural lectin proteins at corresponding position. Both substitutions are expected to retain or enhance the cytotoxicity of the modified protein. In one embodiment, the biological function is "a cytotoxic effect" as defined below. In one embodiment, the substituting amino acid is selected as a favourable amino acid substitution on the basis of a pairwise or a multiple sequence alignment of lectin proteins, preferably fungal lectin proteins.

It is understood that amino acids can be grouped according to different biochemical properties. Examples include: the polar amino acids, the non-polar amino acids, the acidic amino acids and the basic amino acids. In one embodiment, the amino acid used for the amino acid modification is at least one selected from the group consisting of, but not limited to: polar, non-polar, acidic, basic, selenocysteine, pyrrolysine and non-canonical.

The terms "homology" or "homologous" as used herein refer to two or more referenced entities that share at least partial identity over a given region or portion. Areas, regions or domains of homology or identity refer to a portion of two or more referenced entities that share homology or are the same. Thus, where two sequences are identical over one or more sequence regions they share identity in these regions. Substantial homology refers to a molecule that is structurally or functionally conserved such that it has or is predicted to have at least partial structure or function of one or more of the structures or functions (e.g., a biological function or activity) of the reference molecule, or a relevant/corresponding region or portion of the reference molecule to which it shares homology.

In one embodiment, the percentage "homology" between two sequences is determined using the BLASTP algorithm with default parameters (Altschul et al. Nucleic Acids Res. 1997 Sep. 1; 25(17):3389-402). In particular, the BLAST algorithm can be accessed on the internet using the URL: www.blast.ncbi.nlm.nih.gov/Blast.cgi. In an alternative embodiment, for global sequence alignments, percentage homology between two sequences is determined using the EMBOSS Needle algorithm using default parameters. In particular, the EMBOSS Needle algorithm can be accessed on the internet using the URL: www.ebi.ac.uk/Tools/psa/embossneedle/.

Unless otherwise indicated, the term "homology" is used interchangeably with the term "sequence identity" in the present specification.

The term "a corresponding position" as used herein refers to an analogous position between two or more sequences. In one embodiment, the corresponding position is determined through a sequence alignment of at least a first and a second sequence. The corresponding position in the at least first and second sequences is aligned in the output from the sequence alignment and hence can be identified. In one embodiment, the sequence alignment is a pairwise or a multiple sequence alignment. In one embodiment, the sequence alignment is performed by an algorithm. In one embodiment, the algorithm is BLAST or EMBOSS Needle as discussed above.

The term "carbohydrate binding site" as used herein refers to the amino acid residues in a lectin protein that are involved in the recognition and binding of a carbohydrate structure. In one embodiment, the carbohydrate binding site is involved in the recognition and binding of the TF antigen (a disaccharide; Galβ1→3GalNAc-α-Ser/Thr) and/or the Tn antigen (a monosaccharide; GalNAc-α-). In one embodiment, the "carbohydrate binding site" encompasses a "primary carbohydrate binding site" and/or a "secondary carbohydrate binding site".

The term "primary carbohydrate binding site" as used herein refers to one or more amino acid residues which are involved in the recognition and binding a specific carbohydrate structure. In one embodiment, the specific carbohydrate structure is the TF antigen. In one embodiment, the amino acids residues that constitute the primary carbohydrate binding site are selected from one or more of positions 27, 28, 47, 48, 70, 71, 72 and/or 105 in SEQ ID NO. 1 or a corresponding position in a sequence having at least 60% homology thereto. In one embodiment, the corresponding position is determined through a sequence alignment.

The term "secondary carbohydrate binding site" as used herein refers to one or more amino acid residues which are involved in the recognition and binding a specific carbohydrate structure. In one embodiment, the specific carbohydrate structure is the Tn antigen. In one embodiment, the amino acids residues that constitute the secondary carbohydrate binding site are selected from one or more of positions 77, 78, 80, 101, 112 and/or 114 in SEQ ID NO. 1 or a corresponding position in a sequence having at least 60% homology thereto. In one embodiment, the corresponding position is determined through a sequence alignment.

The term "a cytotoxic effect" as used herein refers to a substance which kills cancerous cells or inhibits the growth of cancerous cells (i.e. exerts an antiproliferative activity). In one embodiment, the percentage cytotoxicity of a substance is determined using a Sulforhodadmine B (SRB) assay as detailed in Example 5. In one embodiment, a percentage cytotoxicity of at least 20%, 30%, 40%, 50%, or 60% as determined by the SRB assay is indicative of a cytotoxic effect. In one embodiment, the modified lectin protein has a percentage cytotoxicity that is at least 60%, 70%, 80% or 90% that of a control. In one embodiment, the control is a lectin protein of SEQ ID NO. 1 and in another embodiment the control is SEQ ID NO. 2.

The term "N-terminus" as used herein refers to amino acid residues that are located towards the start of the amino acid sequence (i.e. towards the amino terminus). In one embodiment, the N-terminus refers to the amino acid residues located in the first 10% or 5% of the amino acid sequence.

The term "cleavage of an initiator methionine" as used herein refers to removal of the N-terminal (initiator) methionine from an amino acid sequence. In one embodiment, the cleavage of the initiator methionine is catalysed by the enzyme methionine aminopeptidase (MAP). In one embodiment, cleavage of the initiator methionine is determined using mass spectrometry or HPLC analysis known to a person skilled in the art.

The term "cleavage of an initiator methionine is increased" as used herein refers to an increase in the extent of initiator methionine cleavage relative to a control. In one embodiment, it refers to at least 5%, 10%, 25%, or 50% increase in the extent of initiator methionine cleavage relative to a control. In one embodiment, the control is a lectin protein of SEQ ID NO. 1 and in another embodiment the control is SEQ ID NO. 2.

The term "dimer formation" as used herein refers to the formation of an oligomer containing two monomers that are either identical or non-identical. In one embodiment, dimer formation refers to the production of a dimer containing two modified lectin proteins according to the present invention (either identical or non-identical). In an alternative embodiment, dimer formation refers to the production of a dimer containing a modified lectin protein according to the present invention and an alternative lectin protein, such as one consisting of the sequence of SEQ ID NO. 1. In one embodiment, dimer formation is mediated by a disulphide linkage between cysteine residues in each monomer. In one embodiment, the cysteine residue is at position 76 of SEQ ID NO. 1 or a corresponding position in an amino acid sequence having at least 60% homology thereto. In one embodiment, the corresponding position is determined through a sequence alignment. In one embodiment, the level of dimer formation is determined using any one of mass spectrometry, size exclusion chromatography and/or SDS-PAGE analysis.

The term "reduced dimer formation" as used herein refers to a decrease in the level of dimer formation relative to a control. In one embodiment, "reduced dimer formation" refers to at least 5%, 10%, 25%, or 50% decrease in the level of dimer formation relative to a control. In one embodiment, the control is a lectin protein of SEQ ID NO. 1 and in another embodiment the control is SEQ ID NO. 2.

The term "oxidation" as used herein refers to a loss of electrons or an increase in the oxidation state. In one embodiment, the term "oxidation" refers to oxidation of an amino acid residue, examples of which include methionine, cysteine, tryptophan, tyrosine and/or histidine. In one embodiment, the term "oxidation" refers to oxidation of a methionine residue to methionine sulfoxide. In one embodiment, the methionine residue that is susceptible to oxidation is at position 44 or 89 of SEQ ID NO. 1 or a corresponding position in an amino acid sequence having at least 60% homology thereto. In one embodiment, the corresponding position is determined through a sequence alignment. In one embodiment, the level of oxidation is determined using mass spectrometry and/or reversed phase high-performance liquid chromatography (RP-HPLC). Oxidation is thought to be affecting expression and activity of protein. In one embodiment the effect of oxidation is determined by the effect of substitution of amino acids that are susceptible to oxidation at position 44 or 89 of SEQ ID NO. 1 on the soluble expression and/or activity of the lectin protein.

The term "reduced oxidation" as used herein refers to a decrease in the level of oxidation relative to a control. In one embodiment, "reduced oxidation" refers to an at least 5%, 10%, 25%, or 50% decrease in the level of oxidation relative to a control. In an alternate embodiment "reduced oxidation" refers to enhanced soluble expression and/or activity of lectin protein. In one embodiment, the control is a lectin protein of SEQ ID NO. 1 and in another embodiment the control is SEQ ID NO. 2.

The term "soluble" as used herein refers to the modified lectin protein being expressed in a soluble or at least partially soluble form. In one embodiment, solubility of the modified lectin protein is determined by cell lysis of a host cell that expresses the modified lectin protein and subsequent SDS-PAGE analysis of the lysis supernatant and pellet. The presence of the modified lectin protein in the lysis supernatant indicates that it is soluble. The presence of the modified lectin protein in the lysis supernatant and the pellet indicates that it is partially soluble. In one embodiment, the term "soluble" as used herein refers to the modified lectin protein not forming inclusion bodies. Using the method described above, the presence of the modified lectin protein in the pellet indicates that it is expressed as inclusion bodies.

The term "nucleic acid molecule" as used herein refers to a polymer of multiple nucleotides. The nucleic acid molecules may comprise naturally occurring nucleic acids or may comprise artificial nucleic acids. In one embodiment, the nucleic acid molecule is DNA or a derivative thereof. In an alternative embodiment, the nucleic acid molecule is RNA or a derivative thereof.

The term "nucleotide" as used herein refers to naturally occurring nucleotides and synthetic nucleotide analogues that are recognised by cellular enzymes.

In the quest to develop new lectins with altered and/or improved physico-chemical properties and/or biological activity the inventors of the present invention developed several lectin variants, with modification to the native lectin sequence at active as well as non-active sites.

In one embodiment, the present invention provides recombinant lectin variants derived from the native lectin sequence showing altered properties; preferably showing specificity to certain sugar chains uniquely found on certain cancer cells and/or enhanced solubility and/or stability compared to native protein. These recombinant lectins are obtained by conducting deliberate modifications to the native lectin. In an embodiment of the present invention, the native lectin is derived from the group consisting of, but not limited to, fungus and plants. Typically, the native lectin is derived from a soil borne phytopathogenic fungus. In an exemplary embodiment of the present invention the phytopathogenic fungus is *S. rolfsii*. It is preferred that the recombinant lectins derived from the amino acid sequence of the native lectin have specificity towards Tn antigen and/or TF antigen and hence binds to human colon cancer, ovarian cancer and leukemic cells.

In general terms, the present invention relates to a modified lectin protein comprising an amino acid sequence selected from SEQ ID NO. 1 or an amino acid sequence having at least 60% homology thereto and wherein the modified lectin protein comprises at least one amino acid modification in SEQ ID NO. 1 or in the amino acid sequence having at least 60% homology thereto. The sequence of SEQ ID NO. 1 corresponds to the native *S. rolfsii* lectin sequence (as reported in WO 2010/095143). The amino acid modification is selected from one or more of: an amino acid modification in a carbohydrate binding site of SEQ ID NO. 1 or a sequence having at least 60% homology thereto; an amino acid modification in the N-terminus of SEQ ID NO. 1 or a sequence having at least 60% homology thereto; an amino acid modification that reduces dimer formation of the modified lectin protein; and/or an amino acid modification that reduces oxidation.

It is preferred that the modified lectin protein does not consist of the amino acid sequence of any of SEQ ID NO. 2 (as reported in WO 2010/095143 as the Rec-2 recombinant variant), SEQ ID NO. 3 (as reported in WO 2010/095143 as the Rec-3 recombinant variant) or SEQ ID NO. 4 (as reported in WO 2014/203261). SEQ ID NOS. 2 to 4 are examples of amino acid sequences having at least 60% homology to SEQ ID NO. 1. In particular, SEQ ID NOS. 2, 3 and 4 have a homology of 97.9%, 96.5% and 91.5% to SEQ ID NO. 1 respectively (as determined using EMBOSS Needle).

Carbohydrate Binding Site

In a first embodiment of the present invention, the carbohydrate binding site is a primary carbohydrate binding site that comprises the amino acid positions 27, 28, 47, 48, 70, 71, 72 and 105 in SEQ ID NO. 1 (as reported in Leonidas et al. 2007) or the corresponding positions of a sequence having at least 60% homology to SEQ ID NO. 1. The primary carbohydrate binding site exhibits specificity for the TF antigen (Galβ1→3GalNAc-α-Ser//Thr) which is expressed on the surface of cancer cells. In the first embodiment, the modified lectin protein contains an amino acid substitution at one of more of the positions of the primary binding site. In one embodiment, the modified lectin protein contains an amino acid substitution at one or more positions selected from: 27 and/or 28; 47 and/or 48; 70, 71 and/or 72; and/or 105.

In a second embodiment of the present invention, the carbohydrate binding site is a secondary carbohydrate binding site that comprises the amino acid positions 77, 78, 80, 101, 112 and 114 in SEQ ID NO. 1 (as reported in Leonidas et al. 2007) or the corresponding positions of a sequence having at least 60% homology to SEQ ID NO. 1. The secondary carbohydrate binding site exhibits specificity for the Tn antigen (GalNAc-α-). In the second embodiment, the modified lectin protein contains an amino acid substitution at one or more of the positions of the secondary binding site. In one embodiment, the modified lectin protein contains an amino acid substitution at one or more positions selected from: 77, 78 and/or 80; 101; and/or 112 and/or 114.

It is preferred that an amino acid substitution according to the first and/or second embodiment is a conservative or favourable amino acid substitution. A conservative amino acid substitution refers to the substituting amino acid (i.e. that which replaces the original amino acid) having biochemical properties which are similar to that of the original amino acid. In one embodiment, a polar amino acid is replaced by a different polar amino acid; a non-polar amino acid is replaced by a different non-polar amino acid; an acidic amino acid is replaced by a different acidic amino acid; or a basic amino acid is replaced by a different basic amino acid. It also refers to substitution with amino acid that occurs in maximum natural lectin proteins at corresponding positions based on pairwise or a multiple sequence alignment of lectin proteins. In one embodiment, the modified lectin protein contains a favourable amino acid substitution such that the modified lectin protein preserves a biological function and/or other property of the modified lectin protein. In a preferred embodiment, the modified lectin protein contains a favourable amino acid substitution such that the modified lectin protein retains a cytotoxic effect and/or is soluble. In one embodiment, an amino acid residue is selected for a favourable amino acid substitution based on a pairwise or a multiple sequence alignment of natural lectin proteins, preferably fungal lectin proteins. Favourable substitution is the substitution with amino acid that occurs in few natural lectin proteins at corresponding positions. Without wishing to be bound by theory, it is thought that the selection of an amino acid residue that is present at a corresponding position in a homologous sequence and its inclusion in the modified lectin protein is more likely to maintain a biological function and/or other property (such as the cytotoxic effect and/or solubility) of the modified lectin protein.

In an alternative embodiment, an amino acid substitution according to the first and/or second embodiment is a non-conservative or unfavourable amino acid substitution. A non-conservative or unfavourable amino acid substitution refers to the substituting amino acid (i.e. that which replaces the original amino acid) having biochemical properties which are dissimilar to that of the original amino acid. For example, a polar amino acid is replaced by a non-polar amino acid or vice versa. A non-conservative or unfavourable amino acid substitution also refers to the substitution with amino acid that is not present in the corresponding positions of other natural lectin proteins when aligned pairwise or in multiple sequence. In one embodiment, the non-conservative or unfavourable amino acid substitution alters the cytotoxic effect and/or the solubility of the modified lectin protein with respect to a control. In one embodiment, the altered cytotoxic effect and/or solubility is determined with respect to the lectin protein of SEQ ID NO. 1 and in another embodiment the cytotoxic effect and/or solubility is determined with respect to the lectin protein of SEQ ID NO 2.

In one embodiment, the substituting amino acid in the primary carbohydrate binding site is selected from one or more of:

a. at position 27: conservative, favourable or unfavourable amino acid, wherein the conservative amino acid is non-polar or acidic; favourable is polar or basic and unfavourable amino acid is non-polar;

b. at position 28: conservative, favourable, neutral or unfavourable amino acid, wherein the conservative amino acid is non-polar; favourable is polar, neutral is acidic or basic and unfavourable amino acid is polar;

c. at position 47: unfavourable amino acid, which is basic or non-polar;

d. at position 48: unfavourable amino acid, which is non-polar;

e. at position 70: unfavourable amino acid, which is non-polar;

f. at position 71: unfavourable amino acid, which is non-polar;

g. at position 72: unfavourable amino acid, which is non-polar; and/or h. at position 105: conservative, favourable, neutral or unfavourable amino acid, wherein the conservative amino acid is basic or non-polar; favourable is polar, neutral is acidic, basic or polar and/or unfavourable amino acid is polar, non-polar or acidic.

In particular, the substituting amino acid in the primary carbohydrate binding site is selected from one or more of:

a. glycine (Y27G), tryptophan (Y27W), phenylalanine (Y27F), glutamic acid (Y27E) or histidine (Y27H) at position 27; and/or glycine (A28G), tryptophan (A28W), serine (A28S), aspartic acid (A28D) or histidine (A28H) at position 28;

b. leucine at position 47 (S47L); and/or tryptophan at position 48 (G48W);

c. isoleucine at position 70 (H70I); tryptophan at position 71 (N71W); and/or glycine at position 72 (Y72G); and d. phenylalanine (R105F), glutamine (R105Q), glutamic acid (R105E), leucine (R105L), lysine (R105K), alanine (R105A), serine (R105S), valine (R105V), isoleucine (R105I), proline (R105P), methionine (R105M), glycine (R105G), threonine (R105T), tyrosine (R105Y), tryptophan (R105W), asparagine (R105N), cysteine (R105C), aspartic acid (R105D), or histidine (R105H) at position 105.

In a one embodiment, the substituting amino acid in the secondary carbohydrate binding site is selected from one or more of:
a. at position 77: an unfavourable amino acid which is non-polar;
b. at position 78: an unfavourable amino acid which is non-polar;
c. at position 80: an unfavourable amino acid which is non-polar;
d. at position 101: a favourable, an unfavourable or a neutral amino acid, wherein the favourable amino acid is polar or basic, the unfavourable amino acid is non-polar and the neutral amino acid is non-polar or acidic;
e. at position 112: an unfavourable amino acid which is non-polar;
f. at position 114: an unfavourable amino acid which is polar.

In particular, the substituting amino acid in the secondary carbohydrate binding site is selected from one or more of:
a. phenylalanine at position 77 (D77F), glycine at position 78 (I78G) and tryptophan at position 80 (T80W);
b. phenylalanine (R101F), glutamine (R101Q), methionine (R101M), glutamic acid (R101E); and lysine (R101K) at position 101;
c. glycine at position 112 (Y112G) and/or asparagine at position 114 (V114N).

It is preferred that the modified lectin protein containing an amino acid substitution according to the first and/or second embodiment has a cytotoxic effect. In one embodiment, the cytotoxic effect is determined using a SRB assay. In a particularly preferred embodiment, the modified lectin protein has a percentage cytotoxicity that is higher than or equal to that of a control. In one embodiment, the control is a lectin protein of SEQ ID NO. 1. In an alternative embodiment, the control is a lectin protein other than SEQ ID NO. 1. In one embodiment, the percentage cytotoxicity of the modified lectin protein represents a 20% percentage increase compared with that of the control. In a preferred embodiment, it represents a 45% percentage increase. In alternative embodiments, the percentage cytotoxicity of the modified lectin protein represents at least a 10%, 20%, 30%, 40% or 50%, 60%, 70%, 80%, 90% or 100% increase compared with that of the control. It is also preferred that the modified lectin protein containing an amino acid substitution according to the first and/or second embodiment is soluble or partially soluble.

N-Terminal Modification

In a third embodiment of the present invention, the modified lectin protein comprises an amino acid substitution at position 1 and/or 2 of SEQ ID NO. 1 or a corresponding position of a sequence having at least 60% homology thereto. It is preferred that the substituting amino acid (i.e. that which replaces the original amino acid) at position 1 is not one of valine or threonine. In particular, it is preferred that the substituting amino acid at position 1 has a small side chain. Preferably, the substituting amino acid is selected from one of: alanine, glycine, proline or serine. In a further embodiment, the substituting amino acid at position 2 is tryptophan. In an alternative embodiment, the substituting amino acid at position 2 is a different non-polar amino acid. In one embodiment, the modified lectin protein contains the amino acid substitutions as defined above at positions 1 and 2 of SEQ ID NO. 1 or the corresponding positions of a sequence having at least 60% homology thereto. In a preferred embodiment, the substituting amino acids at positions 1 and 2 are alanine and tryptophan respectively.

It is preferred that the amino acid sequence of the modified lectin protein according to the third embodiment increases cleavage of an N-terminal (initiator) methionine as compared with a control. In one embodiment, the control is an amino acid sequence of SEQ ID NO. 1 and in another embodiment the control is SEQ ID NO. 2. In one embodiment, cleavage of the initiator methionine is catalysed by the enzyme methionine aminopeptidase (MAP). The extent of initiator methionine cleavage is determined using a method known to a person skilled in the art; preferably using mass spectrometry analysis or High Performance Liquid Chromatography (HPLC). Without wishing to be bound by theory, it is believed that the extent of initiator methionine cleavage by MAP is affected by the amino acid residue in the first and/or second position after that of the initiator methionine (e.g. position 1 and/or 2 of SEQ ID NO. 1). In particular, it is thought that an amino acid sequence comprising an amino acid residue with a small side chain at the first position after the initiator methionine increases the extent of initiator methionine cleavage (as discussed above).

Furthermore, it is preferred that the modified lectin protein according to the third embodiment is soluble and/or has a cytotoxic effect. More preferably, the modified lectin protein is soluble and has a cytotoxic effect. In one embodiment, the cytotoxic effect is determined using a SRB assay. In one embodiment, the modified lectin protein exhibits a percentage cytotoxicity that is at least 10%, 20%, 30%, 40%, 50%, 60%, 70%, 80% or 90% of a control. In another embodiment, the modified lectin protein has a percentage cytotoxicity that is less than 10% of a control, or is absent of cytotoxicity. In a further embodiment, the percentage cytotoxicity it is at least 60%, 70%, 80% or 90% that of a lectin protein of SEQ ID NO. 1.

In a variant of the third embodiment, the amino acid substitution in the N-terminus is at a position other than position 1 and/or 2 of SEQ ID NO. 1 or the corresponding position in a sequence having at least 60% homology thereto. In one embodiment, the modified lectin protein contains an amino acid substitution in the first 10% or 5% of the amino acid sequence (other than at positions 1 and/or 2).

Reduced Dimer Formation

The native *S. rolfsii* protein has been reported to exist as a monomer under acidic conditions and to form a dimer at neutral or basic pH (Leonidas et al. 2007). Without wishing to be bound by theory, it is believed that the cysteine residue at position 76 of SEQ ID NO. 1 mediates dimer formation though the formation of a disulphide linkage. In certain embodiments, it is preferable to reduce dimer formation such that only one form of the protein (i.e. the monomeric form) is present.

Thus in a fourth embodiment of the present invention, the modified lectin protein contains an amino acid substitution at position 76 of SEQ ID NO. 1 or a corresponding position of a sequence having at least 60% homology thereto such that the amino acid residue at that position is no longer cysteine. In a preferred embodiment, the substituting amino acid (i.e. that which replaces the original amino acid) at position 76 is glycine. In an alternative embodiment, the substituting amino acid at position 76 is a different non-polar amino acid residue. In one embodiment, the substituting amino acid is selected based on the sequence alignment of fungal lectin proteins as reported in FIG. 6 of Leonidas et al. 2007. Thus in one embodiment, the non-polar substituting amino acid is selected from one of: valine or leucine.

The modified lectin protein containing the amino acid substitution according to the fourth embodiment exhibits reduced dimer formation as compared with a lectin protein of SEQ ID NO. 1. In one embodiment, the level of dimer formation is determined using mass spectrometry. In an alternative embodiment, the level of dimer formation is determined using size exclusion chromatography or SDS-PAGE analysis. It is preferred that the modified lectin protein according to the fourth embodiment is soluble and/or has a cytotoxic effect. More preferably, the modified lectin protein is soluble and has a cytotoxic effect. In one embodiment, the cytotoxic effect is determined using a SRB assay. In one embodiment, the modified lectin protein exhibits a percentage cytotoxicity that is at least 10%, 20%, 30%, 40%, 50%, 60%, 70%, 80% or 90% of a control. In another embodiment, the modified lectin protein has a percentage cytotoxicity that is less than 10% of a control, or is absent of cytotoxicity. In a further embodiment, the percentage cytotoxicity it is at least 60%, 80% or 90% that of a control. In one embodiment, the control is a lectin protein of SEQ ID NO. 1 and in another embodiment the control is SEQ ID NO. 2.

In a variant of the fourth embodiment, the amino acid substitution that reduces dimer formation is at a position other than position 76. For example, without wishing to be bound by theory, in one embodiment, alternative bonds other than a disulphide linkage contribute to dimer formation and an alternative amino acid substitution is employed to disrupt formation of these bonds and hence reduce dimer formation.

Reduced Oxidation

In a fifth embodiment of the present invention, the modified lectin protein contains an amino acid substitution at position 89 of SEQ ID NO. 1 or a corresponding position of an amino acid sequence having at least 60% homology thereto. In a further embodiment, the modified lectin protein contains an amino acid substitution at position 44 and/or 89 of SEQ ID NO. 1 or a corresponding position of an amino acid sequence having at least 60% homology thereto. In a preferred embodiment, the substituting amino acid (i.e. that which replaces the original amino acid) at position 89 is valine. In an alternative embodiment, the substituting amino acid at position 89 is a different non-polar amino acid residue. In one embodiment, the substituting amino acid is selected based on the sequence alignment of fungal lectin proteins as reported in FIG. 6 of Leonidas et al. 2007. Thus in one embodiment, a non-polar amino acid residue selected from one of: leucine or isoleucine. In a further embodiment, the modified lectin protein contains an amino acid substitution at position 44 as per that defined above for position 89. In one embodiment, the modified lectin protein contains an amino acid substitution at positions 44 and 89 as defined above.

Without wishing to be bound by theory, it is thought that the methionine residues at positions 44 and/or 89 of SEQ ID NO. 1 are susceptible to oxidation, which results in formation of methionine sulfoxide at these positions. Oxidation of the methionine residues to methionine sulfoxide has the potential to impair a biological activity of the lectin. Thus in certain embodiments, it is preferable to reduce oxidation of the lectin protein. Accordingly, the modified lectin protein containing the amino acid substitution as defined by the fifth embodiment exhibits reduced oxidation as compared with a lectin protein of SEQ ID NO. 1. In one embodiment, the level of oxidation is determined using mass spectrometry. In an alternative embodiment, the level of oxidation is determined using RP-HPLC. Furthermore, it is preferred that the modified lectin protein according to the fifth embodiment is soluble and/or has a cytotoxic effect. More preferably, the modified lectin protein is soluble and has a cytotoxic effect. In one embodiment, the cytotoxic effect is determined using a SRB assay. In one embodiment, the modified lectin protein exhibits a percentage cytotoxicity that is at least 10%, 20%, 30%, 40%, 50%, 60%, 70%, 80% or 90% of a control. In another embodiment, the modified lectin protein has a percentage cytotoxicity that is less than 10% of a control, or is absent of cytotoxicity. In a further embodiment, the percentage cytotoxicity it is at least 60%, 70% or 90% that of a control. In one embodiment, the control is a lectin protein of SEQ ID NO. 1 and in another embodiment the control is SEQ ID NO. 2.

In a variant of the fifth embodiment, the amino acid substitution that reduces oxidation is at a position other than position 44 and/or 89. For example, without wishing to be bound by theory, in one embodiment, alternative amino acid residues such as cysteine, tryptophan, tyrosine and histidine amino acid residues contribute to the oxidation of the lectin protein. Thus an alternative amino acid substitution is employed to limit oxidation at these sites and hence reduce oxidation of the protein overall.

Further Embodiments

In the first to fifth embodiments described above, the amino acid modification is an amino acid substitution. However, in a variant of any one of the first to fifth embodiments, the amino acid modification is a modification other than an amino acid substitution. In one variant embodiment, the amino acid modification is an addition or a deletion of an amino acid at a particular position in the amino acid sequence. In one embodiment, the addition of an amino acid is the addition of at least 1, 2, 3, 4 or 5 amino acids at a particular position in an amino acid sequence.

In the first to fifth embodiments described above, it is preferred that the modified lectin protein has a cytotoxic effect. In a further embodiment that is relevant to any one of the first to fifth embodiments, the modified lectin has a further biological function (in addition to having a cytotoxic effect). In one embodiment, the biological function relates to the specificity of the modified lectin protein for an antigen.

In the first to fifth embodiments described above, the modified lectin protein may contain an amino acid modification in an amino acid sequence that has at least 60% homology to SEQ ID NO. 1. In a further embodiment that is relevant to any one of the first to fifth embodiments, the amino acid sequence has at least 70%, 75%, 80%, or 85% homology to the amino acid sequence of SEQ ID NO. 1. It is particularly preferred that the amino acid sequence has at least 90%, 95%, 96%, 97%, 98% or 99% homology to the amino acid sequence of SEQ ID NO. 1.

It is to be understood that the modified lectin protein may contain a combination or plurality of any one of the amino acid modifications described above in relation to the first to fifth embodiments.

In a further embodiment of the present invention, there is provided a pharmaceutical composition which comprises a modified lectin protein as described above. In addition, the pharmaceutical composition comprises a pharmaceutically acceptable diluent or excipient. Exemplary diluents and excipients include sterilised water, physiological saline, and phosphate buffer. The pharmaceutical composition, in some embodiments, also comprises a further therapeutic ingredient.

Further details of additional components of the pharmaceutical composition may be found in Remington's Pharmaceutical Sciences and US Pharmacopoeia, 1984, Mack Publishing Company, Easton, PA, USA.

In use, the modified lectin protein, as explained above (hereinafter, the "medicament") is administered to a patient in need of treatment. In one embodiment, a suitable dose for the medicament is from 0.1 to 1 mg/kg. In one embodiment, the patient is suffering from a cancer. In one embodiment, the cancer is selected from one of: ovarian cancer, leukaemia and/or colon cancer. In principle, any mode of administration of the medicament may be used. In one embodiment, the medicament is administered by one of the following modes: injection, spray or inhalation.

In one embodiment, the modified lectin protein as described above is used in the detection of a cancer cell.

In one embodiment, the modified lectin protein as described above is used in a method of diagnosis; preferably, in a method of diagnosis of cancer.

In a further embodiment, the present invention relates to a nucleic acid molecule comprising a nucleotide sequence encoding a modified lectin protein as described above. In one embodiment, the nucleic acid molecule includes any change in the nucleotide sequence including, but not limited to, substitution, deletion, and/or addition.

It is to be appreciated that, owing to the degeneracy of the genetic code, nucleic acid molecules encoding a particular modified lectin variant may have a range of nucleotide sequences. For example, the codons GCA, GCC, GCG and GCT all encode the amino acid alanine.

The nucleic acid molecules may be either DNA or RNA or derivatives thereof.

In one embodiment, the present invention relates to a recombinant DNA molecule comprising a vector. It is preferred that the vector is a plasmid or a viral vector. In one embodiment, there is provided a recombinant vector comprising an insert of nucleic acid molecule comprising a nucleotide sequence encoding a modified lectin as described above. In a further embodiment, the recombinant vector is an expression vector and comprises operatively linked in the 5' to 3' direction: a promoter which functions in a host cell; a structural nucleic acid sequence encoding a modified lectin protein as described above; and a termination signal.

In a further embodiment of the present invention, there is provided a process for producing a recombinant *Sclerotium rolfsii* lectin protein; and, in particular, a modified lectin proteins as described above. In one embodiment, the cloned nucleotide sequences encode modified lectin proteins that are close to the native lectin amino acid sequence, but which provide alternative properties. Alternatively, the nucleotide sequences encoding the modified lectin variants can be synthesised using chemical or recombinant means and expressed in a suitable host to obtain the recombinant proteins. Suitable host cells include prokaryotic cells and both lower eukaryotic cells as well as higher eukaryotic cells. Introduction of the recombinant molecule into the host cells can be effected using methods known in the art. In an exemplary embodiment of the present invention the suitable host is a microbial cell. In a preferred embodiment, the microbial cell is selected from the group consisting of, but not limited to, a yeast cell, *Escherichia* coli, an insect cell line or a mammalian cell line.

The recombinant proteins as described above can be obtained by isolation as an expression product from a recombinant host. The recombinant proteins of the present invention, which in one embodiment, are purified by conventional techniques, typically conventional chromatographic methods. In another exemplary embodiment of the present invention, the molecular mass of the recombinant lectins, is determined by SDS-PAGE, is approximate 16,000 Da. In yet another exemplary embodiment of the present invention the recombinant lectins can possess blood group specificity, typically towards the human blood groups. In still another exemplary embodiment of the present invention the recombinant proteins can have exclusive ability to recognise TF antigen and its cryptic forms.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the present invention will cover any such modifications or embodiments as fall within the true scope of the invention.

EXAMPLES

Example 1: Site Directed Mutagenesis

The amino acid sequence of the native *S. rolfsii* lectin sequence (SEQ ID NO. 1) was modified at the different specific positions as mentioned herein below in the Table 1 through site directed mutagenesis. A plasmid was extracted from *E. coli* BL21 DE3 cells, which encoded the amino acid sequence of the native SRL sequence cloned in a pET20b vector and this was used as the template. A PCR reaction was set up to 50 μl containing 10 μl of 5×Q5 Reaction Buffer, 1 μl of 10 mM dNTPs, 2.5 μl of 1004 Forward primer, 2.5 μl of 1004 Reverse primer, 0.5 μl of Q5 High fidelity DNA polymerase enzyme and 20 ng of template total volume make up to 50 μl with distilled water.

The gene of interest was amplified using PCR with an initial denaturation step at 98° C. for 30 seconds, followed by 35 amplification cycles consisting of a denaturation step at 98° C. for 30 seconds, an annealing step at 55° C. for 30 seconds, and an extension step at 72° C. for 30 seconds. Finally, an additional extension step was carried out at 72° C. for 5 minutes. All the PCR reactions were performed with the Mastercycler Pro. PCR products were analysed on 1.2% agarose gels containing ethidium bromide (EtBr).

TABLE 1

List of primers used for construction different lectin variants derived from the native SRL sequence SEQ ID NO: 1:

| Clone variant | Change | Forward Primer | Reverse Primer |
|---|---|---|---|
| a. Clone variants for efficient cleavage of initiator methionine | | | |
| ULLB-0005/001 | T1S | ATATACATATGAGCTATAAAATTACCG | TATGCTAGTTAT |
| ULLB-0005/002 | T1A | ATATACATATGGCGTATAAAATTACCG | TGCTCAGCGGT |
| ULLB-0005/003 | T1P | ATATACATATGCCGTATAAAATTACCG | |

TABLE 1-continued List of primers used for construction different lectin variants derived from the native SRL sequence SEQ ID NO: 1:

| Clone variant | Change | Forward Primer | Reverse Primer |
|---|---|---|---|
| ULLB-0005/004 | T1G | ATATACATATGGGCTATAAAATTACCG | |
| ULLB-0005/005 | T1A, Y2W | ATATACATATGGCGTGGAAAATTACCG | | b. Clone variants to alter Primary carbohydrate binding site

| Clone variant | Change | Forward Primer | Reverse Primer |
|---|---|---|---|
| ULLB-0005/008 | Y27G, A28W | GTGTGGAAAGGCTGGAATGGCGGTAC | GTACCGCCATTCCAGCCTTTCCACAC |
| ULLB-0005/009 | S47L, G48W | GATGGGTGGTCTGTGGACCAGCGG | CCGCTGGTCCACAGACCACCCATC |
| ULLB-0005/010 | H70I, N71W, Y72G | CCTTTGGTGTGATTTGGGGCAAACGCTGGTG | CACCAGCGTTTGCCCCAAATCACACCAAAGG |
| ULLB-0005/011 | R105F | CGAAGAAGCGTTTGAACGCCAG | CTGGCGTTCAAACGCTTCTTCG | c. Clone variants to alter Secondary carbohydrate binding site

| Clone variant | Change | Forward Primer | Reverse Primer |
|---|---|---|---|
| ULLB-0005/012 | D77F, I78G, T80W | CTGGTGTTTTGGCGTGTGGAACCTGGCAGCGGATGAAAC | CAGGTTCCACACGCCAAAACACCAGCGTTTATAATTATGC |
| ULLB-0005/013 | R101F | GTCAGAAAAACTTTGAAGAAGCGC | GCGCTTCTTCAAAGTTTTTCTGAC |
| ULLB-0005/014 | Y112G, V114N | GGCCAGAACAAAAATGCGAAAGGCCGTAAC | GTTCTGGCCGTTACTCAGCTGGCGTTC | d. Clone variants for prevention of dimer formation and protein oxidation

| Clone variant | Change | Forward Primer | Reverse Primer |
|---|---|---|---|
| ULLB-0005/015 | C76G | CGCTGGGGCGATATTGTGACC | GGTCACAATATCGCCCCAGCG |
| ULLB-0005/016 | M89V | GAAACCGGCGTGGTTATTAATCAG | CTGATTAATAACCACGCCGGTTTC |

Example 2: Restriction Digestion

The PCR products (obtained from example 1) or plasmids were digested with NdeI and BamHI restriction enzyme, using 500 ng of PCR product/plasmid, 1 μl of 10× CutSmart buffer, and 1-2 units of NdeI and 1-2 units of BamHI, to a final volume of 10 μl. The reaction was incubated at 37° C. for 45 minutes to 1 hour, and the results of the digestion was observed on 1.2% agarose gel containing ethidium bromide (EtBr).

The DNA was then extracted and purified from agarose gels.

Example 3: pET Vector Ligation and Confirmation of Transformants by Colony PCR

The ligation reaction to pET vector was carried out using a mixture consisting 100 ng of DNA sample (restriction enzyme-digested product from example 2), 50 ng of digested pET vector, 1 μl of 10×T4 DNA ligase buffer, and 1 μl of T4 DNA ligase enzyme, to a final volume of 10 μl. This reaction was conducted at 22° C. for 1 hour.

The ligation mix was transformed into E. coli DH5a competent cells by heat shock method. The cells were then plated onto LA/Kanamycin plates and incubated overnight at 37° C. The transformants were then subjected to PCR to check the insert integrity and intactness with pET forward and pET reverse primers with following PCR conditions. The PCR program included an initial denaturation step at 95° C. for 10 minutes, followed by 35 amplification cycles consisting of a denaturation step at 95° C. for 30 seconds, an annealing step at 55° C. for 30 seconds, and an extension step at 72° C. for 45 seconds. Finally, an additional extension step was carried out at 72° C. for 10 minutes. The PCR reaction consisted of bacterial colony (DNA template), 10 μM of pET forward primer, 100μ of pET reverse primer, 5 μl of EconoTaq PLUS GREEN 2× Master Mix (Lucigen) and distilled water to a final volume of 10 μl. PCR products were analysed on 1.2% agarose gel containing EtBr.

Example 4: Plasmid DNA Extraction and Expression Analysis

The positive transformants were inoculated into liquid cultures of LB/Kanamycin, and then plasmid DNA extraction was carried out from E. coli. All the constructs prepared in this work, with the inserts in the pET vectors, were confirmed by sequencing.

The pET27b vector containing each modified nucleotide sequence encoding a lectin variant was transformed into E. coli BL 21DE3 GOLD cells. The positive clones were selected by expression analysis in auto-induction medium. The recombinant lectin expression level and size was confirmed by SDS-PAGE analysis. The glycerol stocks of the positive clones were prepared and maintained at −80° C.

The glycerol stock (40 μl) was inoculated into 50 ml LB broth (containing 20 μg/ml kanamycin) and incubated at 37° C. at 140 rpm for 16 hours. 1% culture was inoculated into 200 ml production medium comprising 1% yeast extract (w/v), 1.2% Dextrose (w/v), 0.3% $KH_2PO_4$ (w/v), 1.25% $K_2HPO_4$ (w/v), 0.5% $(NH_4)_2SO_4$ (w/v), 0.05% NaCl (w/v), 0.1% $MgSO_4·7H_2O$ (w/v) and 0.1% (v/v) of trace metal solution. Kanamycin was added at final concentration of 20 μg/ml. The flasks were incubated at 37° C. and at 140 rpm. When $OD_{600}$ of the culture reached to 1.5, the temperature was reduced to 18° C. and the culture was further incubated for 1 hour. The culture was then induced with 0.25 mM IPTG and further incubated at 18° C. for 20 hrs. The culture samples before induction and after induction were analysed for protein expression and solubility by SDS-PAGE analysis. The culture broth was centrifuged at 9000 rpm for 15 minutes at 15° C. The pellet obtained was resuspended in lysis buffer (25 mM tris, 1 mM EDTA, pH 8.0). The cells were lysed by high pressure homogenisation at 18000 psi (124,100 kPa). The lysate was clarified using 0.1 micron hollow fiber pre-equilibrated with lysis buffer.

The clarified protein solution was subjected to ion exchange chromatography to purify the recombinant lectin.

Example 5: Bioassay—Anti-Proliferation Activity of Purified Lectin Against Ovarian Cancer Cell Line (PA-1)

The anti-proliferation activity of the recombinant, purified lectin variants was determined using a Sulforhodamine B (SRB) Assay. The lectin proteins are thought to exert a cytotoxic effect on the PA-1 ovarian cancer cell line through binding to the TF/Tn antigens; thus the assay canal so provide information on the specificity of the lectin proteins. An anti-proliferative activity further indicates stability of the lectin protein as the conformation of the protein is thought to be maintained to retain activity. The assay measured the total biomass by staining cellular proteins with SRB. SRB is a bright-pink amino xanthene dye that can form an electrostatic complex with basic amino acid residues of proteins of trichloroacetic acid fixed cells in slightly acidic conditions. It can dissociate under mild basic conditions and it can be solubilised for measurement. It has been widely used for drug toxicity screening against different types of cancerous and non-cancerous cell lines. The cells were briefly washed, fixed, and stained with the dye. The incorporated dye was then liberated from the cells with Tris base solution. The incorporated dye released from the stained cells was directly proportional to the cell biomass and can be measured to indicate the degree of cytotoxicity caused by the test material.

The cytotoxicity of the cells was monitored/measured when the cells were in the log phase of growth. Tests were performed in a final volume of 200 µl and included a 200 µl control sample of cell free medium to be used as blank absorbance readings. The dilutions of the test were performed in serum free media to reduce background and a 10-fold higher dilution than the desired concentration was prepared.

On the first day, the cells were seeded by an initial trypsinisation step, counted by Trypan blue method in Neuebauer's Chamber and plated in the wells of a flat bottom 96-well plate (dark walled plate) at the density of 5000 cells/well. On the second day, following overnight incubation, the media in the plate was replenished with 180 µL/well and then the cells were treated with 20 µl of each test item at concentrations ranging from 2.5 to 80 µg/ml so that the total volume in each well was 200 µl. The plates were incubated from the second day to the fourth day. The cells were then treated with SRB on the fifth day. The plates were then observed under the microscope under sterile conditions.

The cells were fixed by gently layering 50 µl of 50% trichloroacetic acid (TCA) solution (cold), on top of the growth medium. The plates were not moved after the fixation step so as to avoid dislodging of the cells which results in inaccuracies. These plates were then incubated for 1 hour at 4° C. and then washed with purified water 4 times to remove excess fixative and serum proteins. The plates were air dried. Some of these plates were stored at room temperatures for further use. The plates were then stained with SRB dye by adding 0.4% (50 µl) SRB dye solution to cover the culture surface of the wells followed by incubation for 30 minutes at 28° C.

The stain was then removed by decanting and then rinsed with a wash solution (1% acetic acid). The plates were washed in 5 washing cycles until the unincorporated dye was removed. The plates were further air dried until no moisture was visible.

For solubilisation, 200 µl of SRB Solubilisation Buffer (10 mm Tris) was added to the well i.e. equal to original volume of the well followed by incubation at 28° C. for 5 minutes. The plate was then gently agitated for 5 to 10 minutes to dissolve the dye and absorbance was measured at 580 nm.

Example 6: Amino Acid Modification of the Native S. rolfsii Lectin Sequence

The native lectin sequence was modified to alter the physico-chemical properties as described below.

a) Enhancement of the Efficiency of Cleavage of the Initiator Methionine:

High expression rate of the recombinant proteins in E. coli limits the cleavage of N-terminal methionine (initiator methionine) by methionine amino peptidase (MAP) enzyme, thus resulting in mixture of protein containing Met-lectin and Met-free lectin. One important factor which affects the initiator methionine cleavage is the amino acids following the methionine residue. MAP cleaves all proteins with small side chains on the residue in the second position (i.e. the first amino acid residue after the initiator methionine). Proteins with Valine or Threonine residues after the initiator methionine are much less efficiently cleaved by MAP than those with Alanine, Glycine, Proline, or Serine in this position. Clones were constructed to replace the first (Threonine) and second (Tyrosine) amino acid at N-terminal of the native lectin sequence with 4 different amino acids (Table 2) to check the effect on initiator methionine cleavage, solubility, specificity and biological activity. The solubility, specificity and biological activity of the lectin variants were not affected by the making the changes.

The recombinant lectin was purified from all the five variants of the native lectin sequence designed for efficient methionine cleavage at shake flask level. All the variants of the native lectin sequence, where threonine at position 1 was replaced with alanine, glycine, serine and proline showed soluble and similar expression compared to the control. The biological activity of all the variants was also similar to that of control. It was thus observed that changing the first and/or second amino acid of the lectin sequence does not affect the expression or biological activity as compared to the control.

b) Prevention of Dimer Formation and Protein Oxidation:

The cysteine residues present in the S. rolfsii lectin monomer is thought to contribute to dimer formation by disulfide linkage and hence may affect specificity and biological activity of lectin. The methionine residue in S. rolfsii lectin is thought to be prone to oxidation during the purification process. The cysteine and methionine residues at position 76 and 89 were replaced via an amino acid substitution to prevent the dimer formation and protein oxidation respectively. The ULLB-0005/015 variant of the native lectin sequence where cysteine at position 76 was replaced with glycine in order to prevent the dimer formation expressed recombinant lectin in soluble form without affecting the biological activity as compared with the control. Similarly the ULLB-0005/016 variant of the native lectin sequence where methionine at position 89 was replaced with valine in order to prevent protein oxidation was expressed in soluble form without affecting biological activity compared to the control. Therefore, changing cysteine and methionine at position 76 and 89 with glycine and valine respectively does not affect the expression, solubility, specificity and biological activity of the lectin.

TABLE 2

Summary of clones designed for efficient cleavage of initiator methionine, prevention of dimer formation and protein oxidation (SEQ ID NO: 1)

i. Changes made for efficient cleavage of initiator methionine

| Clone variant | Change in Sequence | Theoretical Mol. Wt. (Dalton) | Theoretical isoelectric point | Expression | Bioassay (PA-1) (% cytotoxicity) | Methionine (Met) content (% Abundance) |
|---|---|---|---|---|---|---|
| Control | TYKIT....... | 16044.73 | 6.47 | Soluble | 31.6-58 | 7.31 |
| ULLB-0005/001 | SYKIT...... | 16029.70 | 6.49 | Soluble | 35.13 | 1.99 |
| ULLB-0005/002 | AYKIT...... | 16013.70 | 6.57 | Soluble | 33.47 | 9.32 |
| ULLB-0005/003 | PYKIT........ | 16039.74 | 6.61 | Soluble | 47.2 | 6.99 |
| ULLB-0005/004 | GYKIT........ | 15999.66 | 6.57 | Soluble | 45 | 1.12 |
| ULLB-0005/005 | AWKIT........ | 16036.74 | 6.57 | Soluble | 34.29 | 15.6 | ii. Changes made for prevention of dimer formation and protein oxidation

| Clone Variant | Change in Sequence | Theoretical Mol. Wt. (Dalton) | Theoretical pI | Expression | Bioassay (PA-1) (% cytotoxicity) |
|---|---|---|---|---|---|
| ULLB-0005/015 | C76G | 15997.64 | 6.47 | Soluble | 30 |
| ULLB-0005/016 | M89V | 16011.67 | 6.47 | Soluble | 34 |
| (Control) | NA | NA | 6.47 | Soluble | 31.6-58 |

The native lectin sequence was also modified to alter the biological activity as described below.

c) Primary Carbohydrate Binding Site Modification:

The primary carbohydrate binding site displays specificity for TF antigen (Galβ1→3GalNAc-α-Ser//Thr) expressed in cancer cells. Amino acids in the primary carbohydrate binding sites were altered and the modified lectin proteins were investigated with regard to protein solubility, specificity and biological activity. With respect to the effect on specificity and biological activity, the cytotoxicity of the modified lectin proteins against an ovarian cancer cell line (PA-1) was assessed. The amino acid modifications made at the primary carbohydrate binding site are illustrated in Table 3. The ULLB-0005/008 (Y27G and A28W) and ULLB-0005/011 (R105F) variants of the native lectin sequence expressed recombinant lectin in soluble form; however, the biological activity was lost. Whereas ULLB-0005/010 (H70I, N71W and Y72G) variant was expressed as partially soluble and the cytotoxicity of this variant was higher than the recombinant lectin in variant ULLB-0005/009 (S47L and G48W) was expressed as inclusion bodies. Therefore, changing the primary carbohydrate binding site affects the solubility as well as the biological activity of the Lectin. The data in this example demonstrate that the amino acid residues at positions 27, 28, 47, 48, 70, 71, 72 and 105 define the primary carbohydrate binding site. It was concluded that the primary carbohydrate binding site is involved in binding with TF antigen which is present on surface of cancerous cells.

TABLE 3

Summary of clones designed to alter the primary carbohydrate binding sites

| Clone variant | Change in amino acid sequence | Theoretical molecular weight | Theoretical isoelectric point | Expression | Bioassay (PA-1) (% cytotoxicity) |
|---|---|---|---|---|---|
| ULLB-0005/008 | Y27G, A28W | 16052.74 | 6.47 | Soluble | No activity |
| ULLB-0005/009 | S47L, G48W | 16198.97 | 6.47 | IB Formed | No activity |
| ULLB-0005/010 | H70I, N71W, Y72G | 15985.73 | 6.38 | Partially Soluble | 52 |
| ULLB-0005/011 | R105F | 16034.72 | 6.16 | Soluble | No Activity |
| Control | Not applicable | 16044.73 | 6.47 | Soluble | 31.6 to 58 | d) Secondary carbohydrate binding site modification:

The secondary carbohydrate binding site involved in binding with GalNAc-α- (Tn antigen) was modified. Amino acids in the secondary carbohydrate binding sites were altered and the modified lectin proteins were investigated with regard to protein solubility, specificity and biological activity. The effect on specificity and biological activity against ovarian cancer cell line (PA-1) was assessed. The amino acids modification carried out at the secondary carbohydrate binding site are depicted in Table 4 and affect the solubility, specificity and/or biological activity of the recombinant lectin.

The secondary binding sites were selected from 77, 78, 80, 101, 112 or 114 and were modified to substitute from D, I, T, R, Y and V to F, G, W, F, G and N, respectively to prepare several new variants from the native lectin sequence. The variants ULLB-0005/012 (D77F, I78G and T80W) and ULLB-0005/014 (Y112G and V114N), which were designed to alter the secondary carbohydrate binding site expressed recombinant lectin in the form of inclusion bodies and partially soluble, respectively. It is possible that an unfavourable amino acid substitution made in ULLB-0005/012 variant contributed to the insoluble expression of this protein. The variant ULLB-0005/013 showed loss of anti-proliferation activity against PA-1 cell line while variant ULLB-0005/014 showed similar anti-proliferation activity compared to control clone against PA-1 cell line. The data in this example demonstrate that the amino acid residues at positions 77, 78, 80, 101, 112 and 114 define the secondary carbohydrate binding site. It was concluded that modifying the secondary carbohydrate binding site affects the solubility as well as biological activity of the lectin.

TABLE 4

Summary of clones designed to alter the secondary carbohydrate binding sites

| Clone variant | Change in sequence | Theoretical molecular weight | Theoretical isoelectric point | Expression | Bioassay (PA-1) (% cytotoxicity) |
|---|---|---|---|---|---|
| ULLB-0005/012 | D77F, I78G, T80W | 16104.82 | 6.90 | IB Formation | Not performed |
| ULLB-0005/013 | R101F | 16034.72 | 6.16 | Soluble | No activity |
| ULLB-0005/014 | Y112G, V114N | 15952.58 | 6.47 | Partially soluble | 42.3 |
| Control | Not applicable | 16044.73 | 6.47 | Soluble | 31.6-58 |

Example 7: New Site Directed Mutagenesis

Similar to Example 1 the amino acid sequence of the variant lectin sequence SEQ ID NO. 2 was modified at the different specific positions as mentioned herein below in the Table 5 through site directed mutagenesis.

TABLE 5

List of primers used for construction different lectin variants derived from the variant lectin sequence SEQ ID NO. 2.

| Clone variant | Change | Forward Primer | Reverse Primer |
|---|---|---|---|
| a. Clone variants to alter Primary carbohydrate binding site | | | |
| ULLB-0005/026 | Y27W | GTGTGGAAATGGGCGAATGGC | GCCATTCGCCCATTTCCACAC |
| ULLB-0005/027 | Y27F | GTGTGGAAATTTGCGAATGGC | GCCATTCGCAAATTTCCACAC |
| ULLB-0005/028 | Y27E | GTGTGGAAAGAAGCGAATGGC | GCCATTCGCTTCTTTCCACAC |
| ULLB-0005/029 | Y27H | GTGTGGAAACATGCGAATGGC | GCCATTCGCATGTTTCCACAC |
| ULLB-0005/030 | A28S | GGAAATATAGCAATGGCGGTACC | GGTACCGCCATTGCTATATTTCC |
| ULLB-0005/031 | A28G | GGAAATATGGCAATGGCGGTACC | GGTACCGCCATTGCCATATTTCC |
| ULLB-0005/032 | A28D | GGAAATATGATAATGGCGGTACC | GGTACCGCCATTATCATATTTCC |
| ULLB-0005/033 | A28H | GGAAATATCATAATGGCGGTACC | GGTACCGCCATTATGATATTTCC |
| ULLB-0005/018 | R105Q | GAAGAAGCGCAGGAACGCCAG | CTGGCGTTCCTGCGCTTCTTC |
| ULLB-0005/019 | R105E | GAAGAAGCGGAAGAACGCCAG | CTGGCGTTCTTCCGCTTCTTC |
| ULLB-0005/020 | R105L | GAAGAAGCGCTGGAACGCCAG | CTGGCGTTCCAGCGCTTCTTC |
| ULLB-0005/021 | R105K | GAAGAAGCGAAAGAACGCCAG | CTGGCGTTCTTTCGCTTCTTC |
| ULLB-0005/034 | R105A | GAAGAAGCGGCGGAACGCCAG | CTGGCGTTCCGCCGCTTCTTC |
| ULLB-0005/035 | R105S | GAAGAAGCGAGCGAACGCCAG | CTGGCGTTCGCTCGCTTCTTC |
| ULLB-0005/036 | R105V | GAAGAAGCGGTGGAACGCCAG | CTGGCGTTCCACCGCTTCTTC |
| ULLB-0005/037 | R105I | GAAGAAGCGATTGAACGCCAG | CTGGCGTTCAATCGCTTCTTC |
| ULLB-0005/038 | R105P | GAAGAAGCGCCGGAACGCCAG | CTGGCGTTCCGGCGCTTCTTC |
| ULLB-0005/039 | R105M | GAAGAAGCGATGGAACGCCAG | CTGGCGTTCCATCGCTTCTTC |
| ULLB-0005/040 | R105G | GAAGAAGCGGGCGAACGCCAG | CTGGCGTTCGCCCGCTTCTTC |
| ULLB-0005/041 | R105T | GAAGAAGCGACCGAACGCCAG | CTGGCGTTCGGTCGCTTCTTC |
| ULLB-0005/042 | R105Y | GAAGAAGCGTATGAACGCCAG | CTGGCGTTCATACGCTTCTTC |
| ULLB-0005/043 | R105W | GAAGAAGCGTGGGAACGCCAG | CTGGCGTTCCCACGCTTCTTC |
| ULLB-0005/044 | R105N | GAAGAAGCGAACGAACGCCAG | CTGGCGTTCGTTCGCTTCTTC |
| ULLB-0005/045 | R105C | GAAGAAGCGTGCGAACGCCAG | CTGGCGTTCGCACGCTTCTTC |

TABLE 5-continued

List of primers used for construction different lectin variants derived from the variant lectin sequence SEQ ID NO. 2.

| Clone variant | Change | Forward Primer | Reverse Primer |
|---|---|---|---|
| ULLB-0005/046 | R105D | GAAGAAGCGGATGAACGCCAG | CTGGCGTTCATCCGCTTCTTC |
| ULLB-0005/047 | R105H | GAAGAAGCGCATGAACGCCAG | CTGGCGTTCATGCGCTTCTTC |
| b. Clone variants to alter Secondary carbohydrate binding site | | | |
| ULLB-0005/022 | R101Q | CAGAAAAACCAGGAAGAAGCGC | GCGCTTCTTCCTGGTTTTTCTG |
| ULLB-0005/023 | R101M | CAGAAAAACATGGAAGAAGCGC | GCGCTTCTTCCATGTTTTTCT

TABLE 6-continued

Summary of clones designed to alter the primary carbohydrate binding sites

| Clone variant | Change in amino acid sequence | Theoretical molecular weight | Theoretical isoelectric point | Expression | Bioassay (PA-1) (% cytotoxicity) |
|---|---|---|---|---|---|
| ULLB-0005/044 | R105N | 16001.64 | 6.16 | Soluble | Not determined |
| ULLB-0005/045 | R105C | 15990.68 | 6.16 | Soluble | No activity |
| ULLB-0005/046 | R105D | 16002.63 | 5.90 | Insoluble | No activity |
| ULLB-0005/047 | R105H | 16024.68 | 6.26 | Soluble | 52 |
| Control | Not applicable | 16044.73 | 6.47 | Soluble | 31.6 to 58 | b. Secondary Carbohydrate Binding Site Modification:

The secondary carbohydrate binding site involved in binding with GalNAc-α- (Tn antigen) was modified. Amino acids in the secondary carbohydrate binding sites were altered and the modified lectin proteins were investigated with regard to protein solubility, specificity and biological activity. The effect on specificity and biological activity against ovarian cancer cell line (PA-1) was assessed. The amino acids modification carried out at the secondary carbohydrate binding site are depicted in Table 7 and affect the solubility, specificity and/or biological activity of the recombinant lectin. The secondary binding site 101 was modified to substitute from R with Q, M, E and K to prepare several new variants from the native lectin sequence. The favourable and neutral substitution at 101 position lead to soluble expression of variants ULLB-0005/022 (R101Q), ULLB-0005/023 (R101M), ULLB-0005/024 (R101E) and ULLB-0005/025 (R101K) and showed similar anti-proliferation activity compared to control clone against PA-1 cell line. The data in this example demonstrate that the amino acid residues at position 101 define the secondary carbohydrate binding site. It was concluded that modifying the secondary carbohydrate binding site leads to soluble expression of recombinant lectin and exhibits biological activity comparable to the control.

TABLE 7

Summary of clones designed to alter the secondary carbohydrate binding sites

| Clone variant | Change in sequence | Theoretical molecular weight | Theoretical isoelectric point | Expression | Bioassay (PA-1) (% cytotoxicity) |
|---|---|---|---|---|---|
| ULLB-0005/022 | R101Q | 16015.67 | 6.16 | Soluble | 44.26 |
| ULLB-0005/023 | R101M | 16018.73 | 6.16 | Soluble | 32.18 |
| ULLB-0005/024 | R101E | 16016.66 | 5.91 | Soluble | 44.21 |
| ULLB-0005/025 | R101K | 16015.72 | 6.47 | Soluble | 38.35 |
| Control | Not applicable | 16044.73 | 6.47 | Soluble | 31.6-8 |

Summary of Sequences

SEQ ID NO. 1:
TYKITVRVYQTNPNAFFHPVEKTVWKYANGGTWTITDDQHVLTMGGSGTSG

TLRFHADNGESFTATFGVHNYKRWCDIVTNLAADETGMVINQQYYSQKNRE

EARERQLSNYEVKNAKGRNFEIVYTEAEGNDLHANLIIG

SEQ ID NO. 2:
TYKITVRVYQTNPDAFFHPVEKTVWKYANGGTWTITDDQHVLTMGGSGTSG

TLRFHADNGESFTATFGVHNYKRWCDIVTNLAADETGMVINQQYYSQKNRE

EARERQLSNYQVKNAKGRNFQIVYTEAEGNDLHANLIIG

SEQ ID NO. 3:
VYKITVRVYQTNPDAFFHPVEKTVWKYANGGTWSITDDQHVLTMGGSGTSG

TLRFHADNGESFTATFGVHNYKRWCDIVTNLAADETGMVINQQYYSQKNRE

EARERQLSNYQVKNAKGRNFQIVYTEAEGNDLHANLIIG

SEQ ID NO. 4:
VYKITVRVYQTNPDAFFHPVEKTVWKYADGGTWSITDDQHVLTMGGSGTSG

TLRFHADNGESFTATFGVHDYKRWCDIVTDLAADETGMVINQEYYSEKDRE

EARERQNSNYEVKDAKGRNFEIVYTEAEGNDLHADLIIG

In this description, reference has been made to multiple approaches to the process, equipment, and systems that constitute this unique, integrated invention and it is understood that many changes and modifications in the described embodiment can be carried out without departing from the scope and the spirit of the invention. The accompanying examples show by way of illustration, specific exemplary approaches of the invention. These approaches are described in sufficient detail to enable those skilled in the art to practice the invention, and it is to be understood that modifications to the various disclosed approaches may be made by a skilled artisan.

Where methods and steps described above indicate certain events occurring in certain order, those of ordinary skill in the art will recognise that the ordering of certain steps may be modified and that such modifications are in accordance with the principles of the invention. Additionally, certain steps may be performed concurrently in a parallel process when possible, as well as performed sequentially.

We claim:

1. A modified lectin protein, wherein the modified lectin protein comprises an amino acid sequence selected from the group consisting of SEQ ID NOs: 5 and 14.

2. A pharmaceutical composition comprising a modified lectin protein as claimed in claim 1 and a pharmaceutically acceptable diluent or excipient and optionally a further therapeutic ingredient.

3. A medicine comprising the pharmaceutical composition according to claim 2.

4. A method of treatment of cancer in a patient comprising administering the pharmaceutical composition according to claim 2 to a patient.

5. A method for treating cancer comprising treating a patient with the modified lectin protein as claimed in claim 1.

6. A method for detecting a cancer cell, diagnosing cancer, and/or providing therapy for cancer comprising treating a patient with the modified lectin protein as claimed in claim 1.

7. A method of treatment of cancer in a patient comprising administering the modified lectin protein as claimed in claim 1.

8. A nucleic acid molecule comprising a nucleotide sequence encoding a modified lectin protein as claimed in claim 1.

9. A recombinant vector comprising the nucleic acid molecule as claimed in claim 8.

10. The recombinant vector as claimed in claim 9 comprising the following operatively linked in a 5' to 3' direction: a promoter which functions in a host cell; the nucleic acid molecule; and a termination signal.

11. The recombinant vector as claimed in claim 9 or 10, wherein the recombinant vector is capable of being replicated, transcribed, translated and/or expressed in a unicellular organism.

12. A transformed host cell comprising the recombinant vector as claimed in claim 9 or 10.

13. The transformed host cell as claimed in claim 12 wherein the host cell is an *Escherichia* coli bacterium or a yeast cell.

14. A method for producing a recombinant *Sclerotium rolfsii* modified lectin protein comprising:
   i) culturing a host cell containing the recombinant vector as claimed in claim 9;
   ii) expressing the recombinant modified lectin protein; and
   iii) isolating the crude recombinant modified lectin protein from the culture.

* * * * *

SEQUENCE LISTING

<160> NUMBER OF SEQ ID NOS: 136

<210> SEQ ID NO 1
<211> LENGTH: 141
<212> TYPE: PRT
<213> ORGANISM: Artificial Sequence
<220> FEATURE:
<223> OTHER INFORMATION: Modified Sequence

<400> SEQUENCE: 1

Thr Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140

<210> SEQ ID NO 2
<211> LENGTH: 141
<212> TYPE: PRT
<213> ORGANISM: Artificial Sequence
<220> FEATURE:
<223> OTHER INFORMATION: Modified Sequence

<400> SEQUENCE: 2

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 3
<211> LENGTH: 141

<212> TYPE: PRT
<213> ORGANISM: Artificial Sequence
<220> FEATURE:
<223> OTHER INFORMATION: Modified Sequence

<400> SEQUENCE: 3

```
Val Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Ser Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140
```

<210> SEQ ID NO 4
<211> LENGTH: 141
<212> TYPE: PRT
<213> ORGANISM: Artificial Sequence
<220> FEATURE:
<223> OTHER INFORMATION: Modified Sequence

<400> SEQUENCE: 4

```
Val Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asp Gly Gly Thr
            20                  25                  30

Trp Ser Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asp Tyr Lys Arg Trp Cys Asp Ile Val Thr
65                  70                  75                  80

Asp Leu Ala Ala Asp Glu Thr Gly Met Val Ile Asn Gln Glu Tyr Tyr
                85                  90                  95

Ser Glu Lys Asp Arg Glu Glu Ala Arg Glu Arg Gln Asn Ser Asn Tyr
            100                 105                 110

Glu Val Lys Asp Ala Lys Gly Arg Asn Phe Glu Ile Val Tyr Thr Glu
        115                 120                 125

Ala Glu Gly Asn Asp Leu His Ala Asp Leu Ile Ile Gly
    130                 135                 140
```

<210> SEQ ID NO 5
<211> LENGTH: 141
<212> TYPE: PRT
<213> ORGANISM: Artificial Sequence
<220> FEATURE:
<223> OTHER INFORMATION: ULLB-0005/001

```
<400> SEQUENCE: 5

Ser Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Gln Leu Ser Asn Tyr
                100                 105                 110

Glu Val Lys Asn Ala Lys Gly Arg Asn Phe Glu Ile Val Tyr Thr Glu
            115                 120                 125

Ala Glu Gly Asn Asp Leu His Ala Asn Leu Ile Ile Gly
        130                 135                 140

<210> SEQ ID NO 6
<211> LENGTH: 27
<212> TYPE: DNA
<213> ORGANISM: Artificial Sequence
<220> FEATURE:
<223> OTHER INFORMATION: ULLB-0005/001 Forward Primer

<400> SEQUENCE: 6
atatacatat gagctataaa attaccg                                        27

<210> SEQ ID NO 7
<211> LENGTH: 23
<212> TYPE: DNA
<213> ORGANISM: Artificial Sequence
<220> FEATURE:
<223> OTHER INFORMATION: ULLB-0005/001 Reverse Primer

<400> SEQUENCE: 7
tatgctagtt attgctcagc ggt                                            23

<210> SEQ ID NO 8
<211> LENGTH: 141
<212> TYPE: PRT
<213> ORGANISM: Artificial Sequence
<220> FEATURE:
<223> OTHER INFORMATION: ULLB-0005/002

<400> SEQUENCE: 8

Ala Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
```

```
                        85                  90                  95

Ser Gln Lys Asn Arg Glu Glu Ala Arg Glu Arg Gln Leu Ser Asn Tyr
                100                 105                 110

Glu Val Lys Asn Ala Lys Gly Arg Asn Phe Glu Ile Val Tyr Thr Glu
            115                 120                 125

Ala Glu Gly Asn Asp Leu His Ala Asn Leu Ile Ile Gly
        130                 135                 140

<210> SEQ ID NO 9
<211> LENGTH: 27
<212> TYPE: DNA
<213> ORGANISM: Artificial Sequence
<220> FEATURE:
<223> OTHER INFORMATION: ULLB-0005/002 Forward Primer

<400> SEQUENCE: 9
atatacatat ggcgtataaa attaccg                                            27

<210> SEQ ID NO 10
<211> LENGTH: 23
<212> TYPE: DNA
<213> ORGANISM: Artificial Sequence
<220> FEATURE:
<223> OTHER INFORMATION: ULLB-0005/002 Reverse Primer

<400> SEQUENCE: 10
tatgctagtt attgctcagc ggt                                                23

<210> SEQ ID NO 11
<211> LENGTH: 141
<212> TYPE: PRT
<213> ORGANISM: Artificial Sequence
<220> FEATURE:
<223> OTHER INFORMATION: ULLB-0005/003

<400> SEQUENCE: 11

Pro Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
                100                 105                 110

Glu Val Lys Asn Ala Lys Gly Arg Asn Phe Glu Ile Val Tyr Thr Glu
            115                 120                 125

Ala Glu Gly Asn Asp Leu His Ala Asn Leu Ile Ile Gly
        130                 135                 140

<210> SEQ ID NO 12
<211> LENGTH: 27
<212> TYPE: DNA
<213> ORGANISM: Artificial Sequence
<220> FEATURE:
<223> OTHER INFORMATION: ULLB-0005/003 Forward Primer
```

<400> SEQUENCE: 12
atatacatat gccgtataaa attaccg					27

<210> SEQ ID NO 13
<211> LENGTH: 23
<212> TYPE: DNA
<213> ORGANISM: Artificial Sequence
<220> FEATURE:
<223> OTHER INFORMATION: ULLB-0005/003 Reverse Primer

<400> SEQUENCE: 13
tatgctagtt attgctcagc ggt					23

<210> SEQ ID NO 14
<211> LENGTH: 141
<212> TYPE: PRT
<213> ORGANISM: Artificial Sequence
<220> FEATURE:
<223> OTHER INFORMATION: ULLB-0005/004

<400> SEQUENCE: 14

```
Gly Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140
```

<210> SEQ ID NO 15
<211> LENGTH: 27
<212> TYPE: DNA
<213> ORGANISM: Artificial Sequence
<220> FEATURE:
<223> OTHER INFORMATION: ULLB-0005/004 Forward Primer

<400> SEQUENCE: 15
atatacatat gggctataaa attaccg					27

<210> SEQ ID NO 16
<211> LENGTH: 23
<212> TYPE: DNA
<213> ORGANISM: Artificial Sequence
<220> FEATURE:
<223> OTHER INFORMATION: ULLB-0005/004 Reverse Primer

<400> SEQUENCE: 16
tatgctagtt attgctcagc ggt					23

<210> SEQ ID NO 17
<211> LENGTH: 141
<212> TYPE: PRT
<213> ORGANISM: Artificial Sequence
<220> FEATURE:
<223> OTHER INFORMATION: ULLB-0005/005

<400> SEQUENCE: 17

```
Ala Trp Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140
```

<210> SEQ ID NO 18
<211> LENGTH: 27
<212> TYPE: DNA
<213> ORGANISM: Artificial Sequence
<220> FEATURE:
<223> OTHER INFORMATION: ULLB-0005/005 Forward Primer

<400> SEQUENCE: 18
atatacatat ggcgtggaaa attaccg                                        27

<210> SEQ ID NO 19
<211> LENGTH: 23
<212> TYPE: DNA
<213> ORGANISM: Artificial Sequence
<220> FEATURE:
<223> OTHER INFORMATION: ULLB-0005/005 Reverse Primer

<400> SEQUENCE: 19
tatgctagtt attgctcagc ggt                                            23

<210> SEQ ID NO 20
<211> LENGTH: 141
<212> TYPE: PRT
<213> ORGANISM: Artificial Sequence
<220> FEATURE:
<223> OTHER INFORMATION: ULLB-0005/008

<400> SEQUENCE: 20

```
Thr Tyr Lys Ile Thr Val Arg Val Tyr Gln Thr Asn Pro Asn Ala Phe
1               5                   10                  15

Phe His Pro Val Glu Lys Thr Val Trp Lys Gly Trp Asn Gly Gly Thr
            20                  25                  30

Trp Thr Ile Thr Asp Asp Gln His Val Leu Thr Met Gly Gly Ser Gly
        35                  40                  45
```

-continued

```
Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
 65                  70                  75                  80

Asn Leu Ala Ala Asp Glu Thr Gly Met Val Ile Asn Gln Gln Tyr Tyr
                 85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140
```

<210> SEQ ID NO 21
<211> LENGTH: 26
<212> TYPE: DNA
<213> ORGANISM: Artificial Sequence
<220> FEATURE:
<223> OTHER INFORMATION: ULLB-0005/008 Forward Primer

<400> SEQUENCE: 21
gtgtggaaag gctggaatgg cggtac                                         26

<210> SEQ ID NO 22
<211> LENGTH: 26
<212> TYPE: DNA
<213> ORGANISM: Artificial Sequence
<220> FEATURE:
<223> OTHER INFORMATION: ULLB-0005/008 Reverse Primer

<400> SEQUENCE: 22
gtaccgccat tccagccttt ccacac                                         26

<210> SEQ ID NO 23
<211> LENGTH: 141
<212> TYPE: PRT
<213> ORGANISM: Artificial Sequence
<220> FEATURE:
<223> OTHER INFORMATION: ULLB-0005/009

<400> SEQUENCE: 23

```
Thr Tyr Lys Ile Thr Val Arg Val Tyr Gln Thr Asn Pro Asn Ala Phe
  1               5                  10                  15

Phe His Pro Val Glu Lys Thr Val Trp Lys Tyr Ala Asn Gly Gly Thr
                 20                  25                  30

Trp Thr Ile Thr Asp Asp Gln His Val Leu Thr Met Gly Gly Leu Trp
             35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
 65                  70                  75                  80

Asn Leu Ala Ala Asp Glu Thr Gly Met Val Ile Asn Gln Gln Tyr Tyr
                 85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140
```

```
<210> SEQ ID NO 24
<211> LENGTH: 24
<212> TYPE: DNA
<213> ORGANISM: Artificial Sequence
<220> FEATURE:
<223> OTHER INFORMATION: ULLB-0005/009 Forward Primer

<400> SEQUENCE: 24
gatgggtggt ctgtggacca gcgg                                          24

<210> SEQ ID NO 25
<211> LENGTH: 24
<212> TYPE: DNA
<213> ORGANISM: Artificial Sequence
<220> FEATURE:
<223> OTHER INFORMATION: ULLB-0005/009 Reverse Primer

<400> SEQUENCE: 25
ccgctggtcc acagaccacc catc                                          24

<210> SEQ ID NO 26
<211> LENGTH: 141
<212> TYPE: PRT
<213> ORGANISM: Artificial Sequence
<220> FEATURE:
<223> OTHER INFORMATION: ULLB-0005/010

<400> SEQUENCE: 26

Thr Tyr Lys Ile Thr Val Arg Val Tyr Gln Thr Asn Pro Asn Ala Phe
 1               5                  10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val Ile Trp Gly Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140

<210> SEQ ID NO 27
<211> LENGTH: 31
<212> TYPE: DNA
<213> ORGANISM: Artificial Sequence
<220> FEATURE:
<223> OTHER INFORMATION: ULLB-0005/010 Forward Primer

<400> SEQUENCE: 27
cctttggtgt gatttggggc aaacgctggt g                                  31

<210> SEQ ID NO 28
<211> LENGTH: 31
<212> TYPE: DNA
<213> ORGANISM: Artificial Sequence
<220> FEATURE:
```

-continued

<223> OTHER INFORMATION: ULLB-0005/010 Reverse Primer

<400> SEQUENCE: 28
caccagcgtt tgccccaaat cacaccaaag g        31

<210> SEQ ID NO 29
<211> LENGTH: 141
<212> TYPE: PRT
<213> ORGANISM: Artificial Sequence
<220> FEATURE:
<223> OTHER INFORMATION: ULLB-0005/011

<400> SEQUENCE: 29

Thr Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Phe Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140

<210> SEQ ID NO 30
<211> LENGTH: 22
<212> TYPE: DNA
<213> ORGANISM: Artificial Sequence
<220> FEATURE:
<223> OTHER INFORMATION: ULLB-0005/011 Forward Primer

<400> SEQUENCE: 30
cgaagaagcg tttgaacgcc ag        22

<210> SEQ ID NO 31
<211> LENGTH: 22
<212> TYPE: DNA
<213> ORGANISM: Artificial Sequence
<220> FEATURE:
<223> OTHER INFORMATION: ULLB-0005/011 Reverse Primer

<400> SEQUENCE: 31
ctggcgttca aacgcttctt cg        22

<210> SEQ ID NO 32
<211> LENGTH: 141
<212> TYPE: PRT
<213> ORGANISM: Artificial Sequence
<220> FEATURE:
<223> OTHER INFORMATION: ULLB-0005/012

<400> SEQUENCE: 32

Thr Tyr Lys Ile Thr Val Arg Val Tyr Gln Thr Asn Pro Asn Ala Phe
1               5                   10                  15

```
Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Phe Gly Val Trp
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140

<210> SEQ ID NO 33
<211> LENGTH: 39
<212> TYPE: DNA
<213> ORGANISM: Artificial Sequence
<220> FEATURE:
<223> OTHER INFORMATION: ULLB-0005/012 Forward Primer

<400> SEQUENCE: 33
ctggtgtttt ggcgtgtgga acctggcagc ggatgaaac                              39

<210> SEQ ID NO 34
<211> LENGTH: 40
<212> TYPE: DNA
<213> ORGANISM: Artificial Sequence
<220> FEATURE:
<223> OTHER INFORMATION: ULLB-0005/012 Reverse Primer

<400> SEQUENCE: 34
caggttccac acgccaaaac accagcgttt ataattatgc                             40

<210> SEQ ID NO 35
<211> LENGTH: 141
<212> TYPE: PRT
<213> ORGANISM: Artificial Sequence
<220> FEATURE:
<223> OTHER INFORMATION: ULLB-0005/013

<400> SEQUENCE: 35

Thr Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Phe Glu Glu Ala Arg Glu Arg Gln Leu Ser Asn Tyr
            100                 105                 110
```

Glu Val Lys Asn Ala Lys Gly Arg Asn Phe Glu Ile Val Tyr Thr Glu
            115                 120                 125
Ala Glu Gly Asn Asp Leu His Ala Asn Leu Ile Ile Gly
        130                 135                 140

<210> SEQ ID NO 36
<211> LENGTH: 24
<212> TYPE: DNA
<213> ORGANISM: Artificial Sequence
<220> FEATURE:
<223> OTHER INFORMATION: ULLB-0005/013 Forward Primer

<400> SEQUENCE: 36
gtcagaaaaa ctttgaagaa gcgc                                          24

<210> SEQ ID NO 37
<211> LENGTH: 24
<212> TYPE: DNA
<213> ORGANISM: Artificial Sequence
<220> FEATURE:
<223> OTHER INFORMATION: ULLB-0005/013 Reverse Primer

<400> SEQUENCE: 37
gcgcttcttc aaagtttttc tgac                                          24

<210> SEQ ID NO 38
<211> LENGTH: 141
<212> TYPE: PRT
<213> ORGANISM: Artificial Sequence
<220> FEATURE:
<223> OTHER INFORMATION: ULLB-0005/014

<400> SEQUENCE: 38

Thr Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Gly
            100                 105                 110

Glu Asn Lys Asn Ala Lys Gly Arg Asn Phe Glu Ile Val Tyr Thr Glu
            115                 120                 125

Ala Glu Gly Asn Asp Leu His Ala Asn Leu Ile Ile Gly
        130                 135                 140

<210> SEQ ID NO 39
<211> LENGTH: 30
<212> TYPE: DNA
<213> ORGANISM: Artificial Sequence
<220> FEATURE:
<223> OTHER INFORMATION: ULLB-0005/014 Forward Primer

<400> SEQUENCE: 39
ggccagaaca aaaatgcgaa aggccgtaac                                    30

-continued

<210> SEQ ID NO 40
<211> LENGTH: 27
<212> TYPE: DNA
<213> ORGANISM: Artificial Sequence
<220> FEATURE:
<223> OTHER INFORMATION: ULLB-0005/014 Reverse Primer

<400> SEQUENCE: 40
gttctggccg ttactcagct ggcgttc                                         27

<210> SEQ ID NO 41
<211> LENGTH: 141
<212> TYPE: PRT
<213> ORGANISM: Artificial Sequence
<220> FEATURE:
<223> OTHER INFORMATION: ULLB-0005/015

<400> SEQUENCE: 41

Thr Tyr Lys Ile Thr Val Arg Val Tyr Gln Thr Asn Pro Asn Ala Phe
1               5                  10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Gly Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140

<210> SEQ ID NO 42
<211> LENGTH: 21
<212> TYPE: DNA
<213> ORGANISM: Artificial Sequence
<220> FEATURE:
<223> OTHER INFORMATION: ULLB-0005/015 Forward Primer

<400> SEQUENCE: 42
cgctggggcg atattgtgac c                                               21

<210> SEQ ID NO 43
<211> LENGTH: 21
<212> TYPE: DNA
<213> ORGANISM: Artificial Sequence
<220> FEATURE:
<223> OTHER INFORMATION: ULLB-0005/015 Reverse Primer

<400> SEQUENCE: 43
ggtcacaata tcgccccagc g                                               21

<210> SEQ ID NO 44
<211> LENGTH: 141
<212> TYPE: PRT
<213> ORGANISM: Artificial Sequence

<220> FEATURE:
<223> OTHER INFORMATION: ULLB-0005/016

<400> SEQUENCE: 44

Thr Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Val Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140

<210> SEQ ID NO 45
<211> LENGTH: 24
<212> TYPE: DNA
<213> ORGANISM: Artificial Sequence
<220> FEATURE:
<223> OTHER INFORMATION: ULLB-0005/016 Forward Primer

<400> SEQUENCE: 45
gaaaccggcg tggttattaa tcag                                      24

<210> SEQ ID NO 46
<211> LENGTH: 24
<212> TYPE: DNA
<213> ORGANISM: Artificial Sequence
<220> FEATURE:
<223> OTHER INFORMATION: ULLB-0005/016 Reverse Primer

<400> SEQUENCE: 46
ctgattaata accacgccgg tttc                                      24

<210> SEQ ID NO 47
<211> LENGTH: 141
<212> TYPE: PRT
<213> ORGANISM: Artificial Sequence
<220> FEATURE:
<223> OTHER INFORMATION: ULLB-0005/018

<400> SEQUENCE: 47

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr

```
                65                  70                  75                  80
Asn Leu Ala Ala Asp Glu Thr Gly Met Val Ile Asn Gln Gln Tyr Tyr
                85                  90                  95

Ser Gln Lys Asn Arg Glu Glu Ala Gln Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 48
<211> LENGTH: 21
<212> TYPE: DNA
<213> ORGANISM: Artificial Sequence
<220> FEATURE:
<223> OTHER INFORMATION: ULLB-0005/018 Forward Primer

<400> SEQUENCE: 48
gaagaagcgc aggaacgcca g                                                21

<210> SEQ ID NO 49
<211> LENGTH: 21
<212> TYPE: DNA
<213> ORGANISM: Artificial Sequence
<220> FEATURE:
<223> OTHER INFORMATION: ULLB-0005/018 Reverse Primer

<400> SEQUENCE: 49
ctggcgttcc tgcgcttctt c                                                21

<210> SEQ ID NO 50
<211> LENGTH: 141
<212> TYPE: PRT
<213> ORGANISM: Artificial Sequence
<220> FEATURE:
<223> OTHER INFORMATION: ULLB-0005/019

<400> SEQUENCE: 50

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Gln Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 51
<211> LENGTH: 21
<212> TYPE: DNA
```

<213> ORGANISM: Artificial Sequence
<220> FEATURE:
<223> OTHER INFORMATION: ULLB-0005/019 Forward Primer

<400> SEQUENCE: 51
gaagaagcgg aagaacgcca g     21

<210> SEQ ID NO 52
<211> LENGTH: 21
<212> TYPE: DNA
<213> ORGANISM: Artificial Sequence
<220> FEATURE:
<223> OTHER INFORMATION: ULLB-0005/019 Reverse Primer

<400> SEQUENCE: 52
ctggcgttct tccgcttctt c     21

<210> SEQ ID NO 53
<211> LENGTH: 141
<212> TYPE: PRT
<213> ORGANISM: Artificial Sequence
<220> FEATURE:
<223> OTHER INFORMATION: ULLB-0005/020

<400> SEQUENCE: 53

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Leu Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 54
<211> LENGTH: 21
<212> TYPE: DNA
<213> ORGANISM: Artificial Sequence
<220> FEATURE:
<223> OTHER INFORMATION: ULLB-0005/020 Forward Primer

<400> SEQUENCE: 54
gaagaagcgc tggaacgcca g     21

<210> SEQ ID NO 55
<211> LENGTH: 21
<212> TYPE: DNA
<213> ORGANISM: Artificial Sequence
<220> FEATURE:
<223> OTHER INFORMATION: ULLB-0005/020 Reverse Primer

<400> SEQUENCE: 55
ctggcgttcc agcgcttctt c                                              21

<210> SEQ ID NO 56
<211> LENGTH: 141
<212> TYPE: PRT
<213> ORGANISM: Artificial Sequence
<220> FEATURE:
<223> OTHER INFORMATION: ULLB-0005/021

<400> SEQUENCE: 56

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Lys Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 57
<211> LENGTH: 21
<212> TYPE: DNA
<213> ORGANISM: Artificial Sequence
<220> FEATURE:
<223> OTHER INFORMATION: ULLB-0005/021 Forward Primer

<400> SEQUENCE: 57
gaagaagcga aagaacgcca g                                              21

<210> SEQ ID NO 58
<211> LENGTH: 21
<212> TYPE: DNA
<213> ORGANISM: Artificial Sequence
<220> FEATURE:
<223> OTHER INFORMATION: ULLB-0005/021 Reverse Primer

<400> SEQUENCE: 58
ctggcgttct ttcgcttctt c                                              21

<210> SEQ ID NO 59
<211> LENGTH: 141
<212> TYPE: PRT
<213> ORGANISM: Artificial Sequence
<220> FEATURE:
<223> OTHER INFORMATION: ULLB-0005/022

<400> SEQUENCE: 59

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
                35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Gln Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 60
<211> LENGTH: 22
<212> TYPE: DNA
<213> ORGANISM: Artificial Sequence
<220> FEATURE:
<223> OTHER INFORMATION: ULLB-0005/022 Forward Primer

<400> SEQUENCE: 60
cagaaaaacc aggaagaagc gc                                          22

<210> SEQ ID NO 61
<211> LENGTH: 22
<212> TYPE: DNA
<213> ORGANISM: Artificial Sequence
<220> FEATURE:
<223> OTHER INFORMATION: ULLB-0005/022 Reverse Primer

<400> SEQUENCE: 61
gcgcttcttc ctggtttttc tg                                          22

<210> SEQ ID NO 62
<211> LENGTH: 141
<212> TYPE: PRT
<213> ORGANISM: Artificial Sequence
<220> FEATURE:
<223> OTHER INFORMATION: ULLB-0005/023

<400> SEQUENCE: 62

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
                35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Met Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

-continued

Ala Glu Gly Asn Asp Leu His Ala Asn Leu Ile Ile Gly
    130                 135                 140

<210> SEQ ID NO 63
<211> LENGTH: 22
<212> TYPE: DNA
<213> ORGANISM: Artificial Sequence
<220> FEATURE:
<223> OTHER INFORMATION: ULLB-0005/023 Forward Primer

<400> SEQUENCE: 63
cagaaaaaca tggaagaagc gc                                        22

<210> SEQ ID NO 64
<211> LENGTH: 22
<212> TYPE: DNA
<213> ORGANISM: Artificial Sequence
<220> FEATURE:
<223> OTHER INFORMATION: ULLB-0005/023 Reverse Primer

<400> SEQUENCE: 64
gcgcttcttc catgtttttc tg                                        22

<210> SEQ ID NO 65
<211> LENGTH: 141
<212> TYPE: PRT
<213> ORGANISM: Artificial Sequence
<220> FEATURE:
<223> OTHER INFORMATION: ULLB-0005/024

<400> SEQUENCE: 65

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Glu Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 66
<211> LENGTH: 22
<212> TYPE: DNA
<213> ORGANISM: Artificial Sequence
<220> FEATURE:
<223> OTHER INFORMATION: ULLB-0005/024 Forward Primer

<400> SEQUENCE: 66
cagaaaaacg aagaagaagc gc                                        22

<210> SEQ ID NO 67
<211> LENGTH: 22

```
<212> TYPE: DNA
<213> ORGANISM: Artificial Sequence
<220> FEATURE:
<223> OTHER INFORMATION: ULLB-0005/024 Reverse Primer

<400> SEQUENCE: 67
gcgcttcttc ttcgtttttc tg                                              22

<210> SEQ ID NO 68
<211> LENGTH: 141
<212> TYPE: PRT
<213> ORGANISM: Artificial Sequence
<220> FEATURE:
<223> OTHER INFORMATION: ULLB-0005/025

<400> SEQUENCE: 68
```

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Lys Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

```
<210> SEQ ID NO 69
<211> LENGTH: 22
<212> TYPE: DNA
<213> ORGANISM: Artificial Sequence
<220> FEATURE:
<223> OTHER INFORMATION: ULLB-0005/025 Forward Primer

<400> SEQUENCE: 69
cagaaaaaca aagaagaagc gc                                              22

<210> SEQ ID NO 70
<211> LENGTH: 22
<212> TYPE: DNA
<213> ORGANISM: Artificial Sequence
<220> FEATURE:
<223> OTHER INFORMATION: ULLB-0005/025 Reverse Primer

<400> SEQUENCE: 70
gcgcttcttc tttgtttttc tg                                              22

<210> SEQ ID NO 71
<211> LENGTH: 141
<212> TYPE: PRT
<213> ORGANISM: Artificial Sequence
<220> FEATURE:
<223> OTHER INFORMATION: ULLB-0005/026

<400> SEQUENCE: 71
```

Thr Tyr Lys Ile Thr Val Arg Val Tyr Gln Thr Asn Pro Asp Ala Phe
1               5                   10                  15

Phe His Pro Val Glu Lys Thr Val Trp Lys Ala Asn Gly Gly Thr
            20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
        130                 135                 140

<210> SEQ ID NO 72
<211> LENGTH: 21
<212> TYPE: DNA
<213> ORGANISM: Artificial Sequence
<220> FEATURE:
<223> OTHER INFORMATION: ULLB-0005/026 Forward Primer

<400> SEQUENCE: 72
gtgtggaaat gggcgaatgg c                                          21

<210> SEQ ID NO 73
<211> LENGTH: 21
<212> TYPE: DNA
<213> ORGANISM: Artificial Sequence
<220> FEATURE:
<223> OTHER INFORMATION: ULLB-0005/026 Reverse Primer

<400> SEQUENCE: 73
gccattcgcc catttccaca c                                          21

<210> SEQ ID NO 74
<211> LENGTH: 141
<212> TYPE: PRT
<213> ORGANISM: Artificial Sequence
<220> FEATURE:
<223> OTHER INFORMATION: ULLB-0005/027

<400> SEQUENCE: 74

Thr Tyr Lys Ile Thr Val Arg Val Tyr Gln Thr Asn Pro Asp Ala Phe
1               5                   10                  15

Phe His Pro Val Glu Lys Thr Val Trp Lys Phe Ala Asn Gly Gly Thr
            20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

```
Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 75
<211> LENGTH: 21
<212> TYPE: DNA
<213> ORGANISM: Artificial Sequence
<220> FEATURE:
<223> OTHER INFORMATION: ULLB-0005/027 Forward Primer

<400> SEQUENCE: 75
gtgtggaaat ttgcgaatgg c                                           21

<210> SEQ ID NO 76
<211> LENGTH: 21
<212> TYPE: DNA
<213> ORGANISM: Artificial Sequence
<220> FEATURE:
<223> OTHER INFORMATION: ULLB-0005/027 Reverse Primer

<400> SEQUENCE: 76
gccattcgca aatttccaca c                                           21

<210> SEQ ID NO 77
<211> LENGTH: 141
<212> TYPE: PRT
<213> ORGANISM: Artificial Sequence
<220> FEATURE:
<223> OTHER INFORMATION: ULLB-0005/028

<400> SEQUENCE: 77

Thr Tyr Lys Ile Thr Val Arg Val Tyr Gln Thr Asn Pro Asp Ala Phe
1               5                   10                  15

Phe His Pro Val Glu Lys Thr Val Trp Lys Glu Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 78
<211> LENGTH: 21
<212> TYPE: DNA
<213> ORGANISM: Artificial Sequence
<220> FEATURE:
<223> OTHER INFORMATION: ULLB-0005/028 Forward Primer
```

<400> SEQUENCE: 78
gtgtggaaag aagcgaatgg c    21

<210> SEQ ID NO 79
<211> LENGTH: 21
<212> TYPE: DNA
<213> ORGANISM: Artificial Sequence
<220> FEATURE:
<223> OTHER INFORMATION: ULLB-0005/028 Reverse Primer

<400> SEQUENCE: 79
gccattcgct tctttccaca c    21

<210> SEQ ID NO 80
<211> LENGTH: 141
<212> TYPE: PRT
<213> ORGANISM: Artificial Sequence
<220> FEATURE:
<223> OTHER INFORMATION: ULLB-0005/029

<400> SEQUENCE: 80

Thr Tyr Lys Ile Thr Val Arg Val Tyr Gln Thr Asn Pro Asp Ala Phe
1               5                   10                  15

Phe His Pro Val Glu Lys Thr Val Trp Lys His Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 81
<211> LENGTH: 21
<212> TYPE: DNA
<213> ORGANISM: Artificial Sequence
<220> FEATURE:
<223> OTHER INFORMATION: ULLB-0005/029 Forward Primer

<400> SEQUENCE: 81
gtgtggaaac atgcgaatgg c    21

<210> SEQ ID NO 82
<211> LENGTH: 21
<212> TYPE: DNA
<213> ORGANISM: Artificial Sequence
<220> FEATURE:
<223> OTHER INFORMATION: ULLB-0005/029 Reverse Primer

<400> SEQUENCE: 82
gccattcgca tgtttccaca c    21

<210> SEQ ID NO 83

-continued

```
<211> LENGTH: 141
<212> TYPE: PRT
<213> ORGANISM: Artificial Sequence
<220> FEATURE:
<223> OTHER INFORMATION: ULLB-0005/030

<400> SEQUENCE: 83

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ser Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 84
<211> LENGTH: 23
<212> TYPE: DNA
<213> ORGANISM: Artificial Sequence
<220> FEATURE:
<223> OTHER INFORMATION: ULLB-0005/030 Forward Primer

<400> SEQUENCE: 84
ggaaatatag caatggcggt acc                                        23

<210> SEQ ID NO 85
<211> LENGTH: 23
<212> TYPE: DNA
<213> ORGANISM: Artificial Sequence
<220> FEATURE:
<223> OTHER INFORMATION: ULLB-0005/030 Reverse Primer

<400> SEQUENCE: 85
ggtaccgcca ttgctatatt tcc                                        23

<210> SEQ ID NO 86
<211> LENGTH: 141
<212> TYPE: PRT
<213> ORGANISM: Artificial Sequence
<220> FEATURE:
<223> OTHER INFORMATION: ULLB-0005/031

<400> SEQUENCE: 86

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Gly Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
```

```
                    50                  55                  60
Ala Thr Phe Gly Val His Asn Tyr Lys Arg Trp Cys Asp Ile Val Thr
 65                  70                  75                  80

Asn Leu Ala Ala Asp Glu Thr Gly Met Val Ile Asn Gln Gln Tyr Tyr
                     85                  90                  95

Ser Gln Lys Asn Arg Glu Glu Ala Arg Glu Arg Gln Leu Ser Asn Tyr
                100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
        130                 135                 140
```

<210> SEQ ID NO 87
<211> LENGTH: 23
<212> TYPE: DNA
<213> ORGANISM: Artificial Sequence
<220> FEATURE:
<223> OTHER INFORMATION: ULLB-0005/031 Forward Primer

<400> SEQUENCE: 87
ggaaatatgg caatggcggt acc        23

<210> SEQ ID NO 88
<211> LENGTH: 23
<212> TYPE: DNA
<213> ORGANISM: Artificial Sequence
<220> FEATURE:
<223> OTHER INFORMATION: ULLB-0005/031 Reverse Primer

<400> SEQUENCE: 88
ggtaccgcca ttgccatatt tcc        23

<210> SEQ ID NO 89
<211> LENGTH: 141
<212> TYPE: PRT
<213> ORGANISM: Artificial Sequence
<220> FEATURE:
<223> OTHER INFORMATION: ULLB-0005/032

<400> SEQUENCE: 89

```
Thr Tyr Lys Ile Thr Val Arg Val Tyr Gln Thr Asn Pro Asp Ala Phe
 1               5                  10                  15

Phe His Pro Val Glu Lys Thr Val Trp Lys Tyr Asp Asn Gly Gly Thr
                 20                  25                  30

Trp Thr Ile Thr Asp Asp Gln His Val Leu Thr Met Gly Gly Ser Gly
             35                  40                  45

Thr Ser Gly Thr Leu Arg Phe His Ala Asp Asn Gly Glu Ser Phe Thr
         50                  55                  60

Ala Thr Phe Gly Val His Asn Tyr Lys Arg Trp Cys Asp Ile Val Thr
 65                  70                  75                  80

Asn Leu Ala Ala Asp Glu Thr Gly Met Val Ile Asn Gln Gln Tyr Tyr
                     85                  90                  95

Ser Gln Lys Asn Arg Glu Glu Ala Arg Glu Arg Gln Leu Ser Asn Tyr
                100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
        130                 135                 140
```

-continued

```
<210> SEQ ID NO 90
<211> LENGTH: 23
<212> TYPE: DNA
<213> ORGANISM: Artificial Sequence
<220> FEATURE:
<223> OTHER INFORMATION: ULLB-0005/032 Forward Primer

<400> SEQUENCE: 90
ggaaatatga taatggcggt acc                                              23

<210> SEQ ID NO 91
<211> LENGTH: 23
<212> TYPE: DNA
<213> ORGANISM: Artificial Sequence
<220> FEATURE:
<223> OTHER INFORMATION: ULLB-0005/032 Reverse Primer

<400> SEQUENCE: 91
ggtaccgcca ttatcatatt tcc                                              23

<210> SEQ ID NO 92
<211> LENGTH: 141
<212> TYPE: PRT
<213> ORGANISM: Artificial Sequence
<220> FEATURE:
<223> OTHER INFORMATION: ULLB-0005/033

<400> SEQUENCE: 92
```

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr His Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

```
<210> SEQ ID NO 93
<211> LENGTH: 23
<212> TYPE: DNA
<213> ORGANISM: Artificial Sequence
<220> FEATURE:
<223> OTHER INFORMATION: ULLB-0005/033 Forward Primer

<400> SEQUENCE: 93
ggaaatatca taatggcggt acc                                              23

<210> SEQ ID NO 94
<211> LENGTH: 23
<212> TYPE: DNA
<213> ORGANISM: Artificial Sequence
<220> FEATURE:
<223> OTHER INFORMATION: ULLB-0005/033 Reverse Primer
```

<400> SEQUENCE: 94
ggtaccgcca ttatgatatt tcc                                            23

<210> SEQ ID NO 95
<211> LENGTH: 141
<212> TYPE: PRT
<213> ORGANISM: Artificial Sequence
<220> FEATURE:
<223> OTHER INFORMATION: ULLB-0005/034

<400> SEQUENCE: 95

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Ala Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 96
<211> LENGTH: 21
<212> TYPE: DNA
<213> ORGANISM: Artificial Sequence
<220> FEATURE:
<223> OTHER INFORMATION: ULLB-0005/034 Forward Primer

<400> SEQUENCE: 96
gaagaagcgg cggaacgcca g                                              21

<210> SEQ ID NO 97
<211> LENGTH: 21
<212> TYPE: DNA
<213> ORGANISM: Artificial Sequence
<220> FEATURE:
<223> OTHER INFORMATION: ULLB-0005/034 Reverse Primer

<400> SEQUENCE: 97
ctggcgttcc gccgcttctt c                                              21

<210> SEQ ID NO 98
<211> LENGTH: 141
<212> TYPE: PRT
<213> ORGANISM: Artificial Sequence
<220> FEATURE:
<223> OTHER INFORMATION: ULLB-0005/035

<400> SEQUENCE: 98

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Ser Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 99
<211> LENGTH: 21
<212> TYPE: DNA
<213> ORGANISM: Artificial Sequence
<220> FEATURE:
<223> OTHER INFORMATION: ULLB-0005/035 Forward Primer

<400> SEQUENCE: 99
gaagaagcga gcgaacgcca g                                        21

<210> SEQ ID NO 100
<211> LENGTH: 21
<212> TYPE: DNA
<213> ORGANISM: Artificial Sequence
<220> FEATURE:
<223> OTHER INFORMATION: ULLB-0005/035 Reverse Primer

<400> SEQUENCE: 100
ctggcgttcg ctcgcttctt c                                        21

<210> SEQ ID NO 101
<211> LENGTH: 141
<212> TYPE: PRT
<213> ORGANISM: Artificial Sequence
<220> FEATURE:
<223> OTHER INFORMATION: ULLB-0005/036

<400> SEQUENCE: 101

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Val Glu Arg Gln Leu Ser Asn Tyr
            100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
    130                 135                 140

<210> SEQ ID NO 102
<211> LENGTH: 21
<212> TYPE: DNA
<213> ORGANISM: Artificial Sequence
<220> FEATURE:
<223> OTHER INFORMATION: ULLB-0005/036 Forward Primer

<400> SEQUENCE: 102
gaagaagcgg tggaacgcca g                                              21

<210> SEQ ID NO 103
<211> LENGTH: 21
<212> TYPE: DNA
<213> ORGANISM: Artificial Sequence
<220> FEATURE:
<223> OTHER INFORMATION: ULLB-0005/036 Reverse Primer

<400> SEQUENCE: 103
ctggcgttcc accgcttctt c                                              21

<210> SEQ ID NO 104
<211> LENGTH: 141
<212> TYPE: PRT
<213> ORGANISM: Artificial Sequence
<220> FEATURE:
<223> OTHER INFORMATION: ULLB-0005/037

<400> SEQUENCE: 104

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Ile Glu Arg Gln Leu Ser Asn Tyr
            100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
    130                 135                 140

<210> SEQ ID NO 105
<211> LENGTH: 21
<212> TYPE: DNA
<213> ORGANISM: Artificial Sequence
<220> FEATURE:
<223> OTHER INFORMATION: ULLB-0005/037 Forward Primer

<400> SEQUENCE: 105
gaagaagcga ttgaacgcca g                                              21

```
<210> SEQ ID NO 106
<211> LENGTH: 21
<212> TYPE: DNA
<213> ORGANISM: Artificial Sequence
<220> FEATURE:
<223> OTHER INFORMATION: ULLB-0005/037 Reverse Primer

<400> SEQUENCE: 106
ctggcgttca atcgcttctt c                                          21

<210> SEQ ID NO 107
<211> LENGTH: 141
<212> TYPE: PRT
<213> ORGANISM: Artificial Sequence
<220> FEATURE:
<223> OTHER INFORMATION: ULLB-0005/038

<400> SEQUENCE: 107
```

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Pro Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

```
<210> SEQ ID NO 108
<211> LENGTH: 21
<212> TYPE: DNA
<213> ORGANISM: Artificial Sequence
<220> FEATURE:
<223> OTHER INFORMATION: ULLB-0005/038 Forward Primer

<400> SEQUENCE: 108
gaagaagcgc cggaacgcca g                                          21

<210> SEQ ID NO 109
<211> LENGTH: 21
<212> TYPE: DNA
<213> ORGANISM: Artificial Sequence
<220> FEATURE:
<223> OTHER INFORMATION: ULLB-0005/038 Reverse Primer

<400> SEQUENCE: 109
ctggcgttcc ggcgcttctt c                                          21

<210> SEQ ID NO 110
<211> LENGTH: 141
<212> TYPE: PRT
<213> ORGANISM: Artificial Sequence
<220> FEATURE:
```

<223> OTHER INFORMATION: ULLB-0005/039

<400> SEQUENCE: 110

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Met Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 111
<211> LENGTH: 21
<212> TYPE: DNA
<213> ORGANISM: Artificial Sequence
<220> FEATURE:
<223> OTHER INFORMATION: ULLB-0005/039 Forward Primer

<400> SEQUENCE: 111
gaagaagcga tggaacgcca g                                             21

<210> SEQ ID NO 112
<211> LENGTH: 21
<212> TYPE: DNA
<213> ORGANISM: Artificial Sequence
<220> FEATURE:
<223> OTHER INFORMATION: ULLB-0005/039 Reverse Primer

<400> SEQUENCE: 112
ctggcgttcc atcgcttctt c                                             21

<210> SEQ ID NO 113
<211> LENGTH: 141
<212> TYPE: PRT
<213> ORGANISM: Artificial Sequence
<220> FEATURE:
<223> OTHER INFORMATION: ULLB-0005/040

<400> SEQUENCE: 113

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
            85                  90                  95

Ser Gln Lys Asn Arg Glu Glu Ala Gly Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 114
<211> LENGTH: 21
<212> TYPE: DNA
<213> ORGANISM: Artificial Sequence
<220> FEATURE:
<223> OTHER INFORMATION: ULLB-0005/040 Forward Primer

<400> SEQUENCE: 114
gaagaagcgg gcgaacgcca g                                             21

<210> SEQ ID NO 115
<211> LENGTH: 21
<212> TYPE: DNA
<213> ORGANISM: Artificial Sequence
<220> FEATURE:
<223> OTHER INFORMATION: ULLB-0005/040 Reverse Primer

<400> SEQUENCE: 115
ctggcgttcg cccgcttctt c                                             21

<210> SEQ ID NO 116
<211> LENGTH: 141
<212> TYPE: PRT
<213> ORGANISM: Artificial Sequence
<220> FEATURE:
<223> OTHER INFORMATION: ULLB-0005/041

<400> SEQUENCE: 116

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
            85                  90                  95

Ser Gln Lys Asn Arg Glu Glu Ala Thr Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 117
<211> LENGTH: 21
<212> TYPE: DNA
<213> ORGANISM: Artificial Sequence

```
<220> FEATURE:
<223> OTHER INFORMATION: ULLB-0005/041 Forward Primer

<400> SEQUENCE: 117
gaagaagcga ccgaacgcca g                                              21

<210> SEQ ID NO 118
<211> LENGTH: 21
<212> TYPE: DNA
<213> ORGANISM: Artificial Sequence
<220> FEATURE:
<223> OTHER INFORMATION: ULLB-0005/041 Reverse Primer

<400> SEQUENCE: 118
ctggcgttcg gtcgcttctt c                                              21

<210> SEQ ID NO 119
<211> LENGTH: 141
<212> TYPE: PRT
<213> ORGANISM: Artificial Sequence
<220> FEATURE:
<223> OTHER INFORMATION: ULLB-0005/042

<400> SEQUENCE: 119
```

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Tyr Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

```
<210> SEQ ID NO 120
<211> LENGTH: 21
<212> TYPE: DNA
<213> ORGANISM: Artificial Sequence
<220> FEATURE:
<223> OTHER INFORMATION: ULLB-0005/042 Forward Primer

<400> SEQUENCE: 120
gaagaagcgt atgaacgcca g                                              21

<210> SEQ ID NO 121
<211> LENGTH: 21
<212> TYPE: DNA
<213> ORGANISM: Artificial Sequence
<220> FEATURE:
<223> OTHER INFORMATION: ULLB-0005/042 Reverse Primer

<400> SEQUENCE: 121
ctggcgttca tacgcttctt c                                              21
```

<210> SEQ ID NO 122
<211> LENGTH: 141
<212> TYPE: PRT
<213> ORGANISM: Artificial Sequence
<220> FEATURE:
<223> OTHER INFORMATION: ULLB-0005/043

<400> SEQUENCE: 122

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Trp Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 123
<211> LENGTH: 21
<212> TYPE: DNA
<213> ORGANISM: Artificial Sequence
<220> FEATURE:
<223> OTHER INFORMATION: ULLB-0005/043 Forward Primer

<400> SEQUENCE: 123
gaagaagcgt gggaacgcca g                                         21

<210> SEQ ID NO 124
<211> LENGTH: 21
<212> TYPE: DNA
<213> ORGANISM: Artificial Sequence
<220> FEATURE:
<223> OTHER INFORMATION: ULLB-0005/043 Reverse Primer

<400> SEQUENCE: 124
ctggcgttcc cacgcttctt c                                         21

<210> SEQ ID NO 125
<211> LENGTH: 141
<212> TYPE: PRT
<213> ORGANISM: Artificial Sequence
<220> FEATURE:
<223> OTHER INFORMATION: ULLB-0005/044

<400> SEQUENCE: 125

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly

```
                35                  40                  45
Thr Ser Gly Thr Leu Arg Phe His Ala Asp Asn Gly Glu Ser Phe Thr
 50                  55                  60

Ala Thr Phe Gly Val His Asn Tyr Lys Arg Trp Cys Asp Ile Val Thr
 65                  70                  75                  80

Asn Leu Ala Ala Asp Glu Thr Gly Met Val Ile Asn Gln Gln Tyr Tyr
                 85                  90                  95

Ser Gln Lys Asn Arg Glu Glu Ala Asn Glu Arg Gln Leu Ser Asn Tyr
                100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
        130                 135                 140

<210> SEQ ID NO 126
<211> LENGTH: 21
<212> TYPE: DNA
<213> ORGANISM: Artificial Sequence
<220> FEATURE:
<223> OTHER INFORMATION: ULLB-0005/044 Forward Primer

<400> SEQUENCE: 126
gaagaagcga acgaacgcca g                                        21

<210> SEQ ID NO 127
<211> LENGTH: 21
<212> TYPE: DNA
<213> ORGANISM: Artificial Sequence
<220> FEATURE:
<223> OTHER INFORMATION: ULLB-0005/044 Reverse Primer

<400> SEQUENCE: 127
ctggcgttcg ttcgcttctt c                                        21

<210> SEQ ID NO 128
<211> LENGTH: 141
<212> TYPE: PRT
<213> ORGANISM: Artificial Sequence
<220> FEATURE:
<223> OTHER INFORMATION: ULLB-0005/045

<400> SEQUENCE: 128

Thr Tyr Lys Ile Thr Val Arg Val Tyr Gln Thr Asn Pro Asp Ala Phe
 1               5                  10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
         35                  40                  45

Thr Ser Gly Thr Leu Arg Phe His Ala Asp Asn Gly Glu Ser Phe Thr
 50                  55                  60

Ala Thr Phe Gly Val His Asn Tyr Lys Arg Trp Cys Asp Ile Val Thr
 65                  70                  75                  80

Asn Leu Ala Ala Asp Glu Thr Gly Met Val Ile Asn Gln Gln Tyr Tyr
                 85                  90                  95

Ser Gln Lys Asn Arg Glu Glu Ala Cys Glu Arg Gln Leu Ser Asn Tyr
                100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
```

-continued

```
<210> SEQ ID NO 129
<211> LENGTH: 21
<212> TYPE: DNA
<213> ORGANISM: Artificial Sequence
<220> FEATURE:
<223> OTHER INFORMATION: ULLB-0005/045 Forward Primer

<400> SEQUENCE: 129
gaagaagcgt gcgaacgcca g                                     21

<210> SEQ ID NO 130
<211> LENGTH: 21
<212> TYPE: DNA
<213> ORGANISM: Artificial Sequence
<220> FEATURE:
<223> OTHER INFORMATION: ULLB-0005/045 Reverse Primer

<400> SEQUENCE: 130
ctggcgttcg cacgcttctt c                                     21

<210> SEQ ID NO 131
<211> LENGTH: 141
<212> TYPE: PRT
<213> ORGANISM: Artificial Sequence
<220> FEATURE:
<223> OTHER INFORMATION: ULLB-0005/046

<400> SEQUENCE: 131
```

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Asp Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

```
<210> SEQ ID NO 132
<211> LENGTH: 21
<212> TYPE: DNA
<213> ORGANISM: Artificial Sequence
<220> FEATURE:
<223> OTHER INFORMATION: ULLB-0005/046 Forward Primer

<400> SEQUENCE: 132
gaagaagcgg atgaacgcca g                                     21

<210> SEQ ID NO 133
<211> LENGTH: 21
<212> TYPE: DNA
```

```
<213> ORGANISM: Artificial Sequence
<220> FEATURE:
<223> OTHER INFORMATION: ULLB-0005/046 Reverse Primer

<400> SEQUENCE: 133
ctggcgttca tccgcttctt c                                              21

<210> SEQ ID NO 134
<211> LENGTH: 141
<212> TYPE: PRT
<213> ORGANISM: Artificial Sequence
<220> FEATURE:
<223> OTHER INFORMATION: ULLB-0005/047

<400> SEQUENCE: 134

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Tyr Tyr
                85                  90                  95

Ser Gln Lys Asn Arg Glu Glu Ala His Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 135
<211> LENGTH: 21
<212> TYPE: DNA
<213> ORGANISM: Artificial Sequence
<220> FEATURE:
<223> OTHER INFORMATION: ULLB-0005/047 Forward Primer

<400> SEQUENCE: 135
gaagaagcgc atgaacgcca g                                              21

<210> SEQ ID NO 136
<211> LENGTH: 21
<212> TYPE: DNA
<213> ORGANISM: Artificial Sequence
<220> FEATURE:
<223> OTHER INFORMATION: ULLB-0005/047 Reverse Primer

<400> SEQUENCE: 136
ctggcgttca tgcgcttctt c                                              21
```